US011517682B2

(12) United States Patent
Varga et al.

(10) Patent No.: US 11,517,682 B2
(45) Date of Patent: Dec. 6, 2022

(54) APPARATUS AND METHODS FOR INTRAVENOUS GAS ELIMINATION

(71) Applicant: VITAL SIGNS, INC., San Diego, CA (US)

(72) Inventors: Christopher Varga, Laguna Hills, CA (US); Jason Anthony Mohr, Fontana, CA (US); Megan Danielle Friedlander, San Diego, CA (US); Carlos Aceves Mendoza, Anaheim, CA (US)

(73) Assignee: VITAL SIGNS, INC., San Diego, CA (US)

( * ) Notice: Subject to any disclaimer, the term of this patent is extended or adjusted under 35 U.S.C. 154(b) by 1022 days.

(21) Appl. No.: 16/304,107

(22) PCT Filed: May 25, 2017

(86) PCT No.: PCT/US2017/034474
§ 371 (c)(1),
(2) Date: Nov. 21, 2018

(87) PCT Pub. No.: WO2017/205625
PCT Pub. Date: Nov. 30, 2017

(65) Prior Publication Data
US 2020/0324059 A1    Oct. 15, 2020

Related U.S. Application Data

(63) Continuation of application No. 15/167,914, filed on May 27, 2016, now Pat. No. 10,179,213, which is a
(Continued)

(51) Int. Cl.
*A61M 5/38* (2006.01)
*A61M 5/168* (2006.01)
(Continued)

(52) U.S. Cl.
CPC ............ *A61M 5/385* (2013.01); *A61M 5/142* (2013.01); *A61M 5/16813* (2013.01);
(Continued)

(58) Field of Classification Search
CPC .. A61M 39/22; A61M 5/142; A61M 5/16813; A61M 5/16818; A61M 5/365;
(Continued)

(56) References Cited

U.S. PATENT DOCUMENTS 2,489,966 A * 11/1949 Laure .................... A61M 5/165
604/406
3,785,380 A * 1/1974 Brumfield ............... A61M 1/76
604/902
(Continued)

FOREIGN PATENT DOCUMENTS

CN    101547674 A    9/2009
CN    205073394 U    3/2016
(Continued)

OTHER PUBLICATIONS

US 9,314,372 B2, 04/2016, Grevin et al. (withdrawn)
(Continued)

*Primary Examiner* — Quynh-Nhu H. Vu
(74) *Attorney, Agent, or Firm* — Morgan, Lewis & Bockius LLP

(57) ABSTRACT

A gas elimination apparatus and a method for use in an intravenous delivery system are provided. The apparatus includes in a fluid inlet coupling a fluid flow into a liquid chamber, a fluid outlet protruding into the liquid chamber, and a flow diversion member proximal to the fluid outlet. The flow diversion member configured to block a direct flow between the fluid inlet and the fluid outlet. The apparatus includes a membrane separating a portion of the liquid chamber from an outer chamber and a gas venting valve
(Continued)

fluidically coupling the outer chamber with the atmosphere. The flow diversion member may be mechanically supported by at least one strut or elongate member extending along a flow direction into the liquid chamber.

13 Claims, 22 Drawing Sheets

Related U.S. Application Data continuation-in-part of application No. 14/723,415, filed on May 27, 2015, now abandoned.

(51) Int. Cl.
  *A61M 5/142* (2006.01)
  *A61M 39/22* (2006.01)
  *A61M 5/36* (2006.01)

(52) U.S. Cl.
  CPC ........ *A61M 5/16818* (2013.01); *A61M 39/22* (2013.01); *A61M 5/365* (2013.01); *A61M 2205/3592* (2013.01); *A61M 2205/52* (2013.01)

(58) Field of Classification Search
  CPC .......... A61M 5/36; A61M 5/38; A61M 5/385; A61M 1/3627; B01D 19/0042
  See application file for complete search history.

(56) References Cited

U.S. PATENT DOCUMENTS

| | | | | |
|---|---|---|---|---|
| 3,870,637 A | * | 3/1975 | Miyoshi | B01D 53/22 210/243 |
| 3,954,623 A | * | 5/1976 | Hammer | B01D 36/001 215/261 |
| 3,993,062 A | * | 11/1976 | Jess | F16K 7/10 96/219 |
| 4,013,072 A | * | 3/1977 | Jess | A61M 5/165 137/197 |
| 4,013,073 A | * | 3/1977 | Cunningham | B65D 35/247 604/212 |
| 4,031,891 A | * | 6/1977 | Jess | B01D 19/0031 604/126 |
| 4,038,194 A | * | 7/1977 | Luceyk | B01D 27/08 210/493.2 |
| 4,045,851 A | * | 9/1977 | Ashare | B01D 63/02 210/321.89 |
| 4,116,646 A | | 9/1978 | Edwards | |
| 4,175,558 A | | 11/1979 | Hess, III et al. | |
| 4,214,883 A | | 7/1980 | Raseley et al. | |
| 4,276,170 A | * | 6/1981 | Vaillancourt | A61M 5/165 96/6 |
| 4,283,289 A | * | 8/1981 | Meyst | B01D 29/33 210/450 |
| 4,306,972 A | * | 12/1981 | Denti | B01D 63/02 210/450 |
| 4,411,783 A | * | 10/1983 | Dickens | B01D 29/908 210/450 |
| 4,707,268 A | * | 11/1987 | Shah | B01D 63/04 210/650 |
| 4,758,341 A | * | 7/1988 | Banner | B01D 65/00 210/232 |
| 4,801,292 A | * | 1/1989 | Watson | A61M 3/0229 604/185 |
| 4,824,566 A | * | 4/1989 | Thibos | B01D 63/021 210/497.1 |
| 4,976,754 A | * | 12/1990 | Edelstein | B01D 19/0031 96/219 |
| 4,985,055 A | * | 1/1991 | Thorne | A61B 5/097 128/205.12 |
| 5,045,096 A | | 9/1991 | Quang et al. | |
| 5,779,674 A | * | 7/1998 | Ford | A61M 5/38 604/122 |
| 6,013,060 A | | 1/2000 | Woodard | |
| 6,013,061 A | | 1/2000 | Kelley | |
| 6,193,689 B1 | | 2/2001 | Woodard | |
| 6,508,859 B1 | | 1/2003 | Zia et al. | |
| 6,669,762 B2 | * | 12/2003 | Hirayama | B01D 19/0031 96/219 |
| 6,746,514 B2 | | 6/2004 | Bedingfield et al. | |
| 7,097,690 B2 | | 8/2006 | Usher et al. | |
| 7,172,696 B1 | * | 2/2007 | Martinez | B01D 63/025 96/10 |
| 7,238,224 B2 | | 7/2007 | Kent | |
| 7,279,031 B1 | * | 10/2007 | Wright | A61M 1/3627 96/197 |
| 7,316,662 B2 | | 1/2008 | Delnevo et al. | |
| 7,422,565 B2 | | 9/2008 | Delnevo et al. | |
| 7,547,295 B2 | | 6/2009 | Cassidy | |
| 7,722,577 B2 | | 5/2010 | Miner | |
| 8,038,663 B2 | | 10/2011 | Miner | |
| 8,192,534 B2 | * | 6/2012 | Hekmat | A61M 1/3627 96/155 |
| 8,282,608 B2 | | 10/2012 | Miner et al. | |
| 8,308,856 B2 | | 11/2012 | Brueckner et al. | |
| 8,337,701 B2 | | 12/2012 | Martin et al. | |
| 8,444,586 B2 | | 5/2013 | Beck | |
| 8,523,829 B2 | | 9/2013 | Miner et al. | |
| 8,540,807 B2 | | 9/2013 | Crowder et al. | |
| 8,540,808 B2 | | 9/2013 | Crowder et al. | |
| 8,632,624 B2 | | 1/2014 | Cassidy et al. | |
| 9,173,987 B2 | | 11/2015 | Meyer et al. | |
| 9,233,198 B2 | | 1/2016 | Cassidy et al. | |
| 9,345,616 B2 | | 5/2016 | Grevin et al. | |
| 10,179,213 B2 | * | 1/2019 | Varga | A61M 5/16818 |
| 10,786,631 B2 | * | 9/2020 | Varga | A61M 5/385 |
| 2005/0077225 A1 | | 4/2005 | Usher et al. | |
| 2005/0171491 A1 | | 8/2005 | Minh Miner | |
| 2010/0212407 A1 | | 8/2010 | Stringham et al. | |
| 2013/0092640 A1 | * | 4/2013 | Cassidy | A61M 1/0281 210/801 |
| 2013/0245545 A1 | | 9/2013 | Arnold | |
| 2014/0350511 A1 | | 11/2014 | Carlisle et al. | |
| 2015/0015645 A1 | | 1/2015 | Bui | |
| 2015/0328429 A1 | | 11/2015 | Acker | |
| 2016/0030293 A1 | | 2/2016 | Dorsey et al. | |
| 2016/0095986 A1 | | 4/2016 | Cassidy et al. | |
| 2016/0213862 A1 | | 7/2016 | Whitaker et al. | |
| 2016/0346485 A1 | | 12/2016 | Mohr et al. | |
| 2016/0346486 A1 | | 12/2016 | Varga et al. | |
| 2020/0368454 A1 | * | 11/2020 | Varga | A61M 39/22 |

FOREIGN PATENT DOCUMENTS

| | | |
|---|---|---|
| CN | 107666922 A | 2/2018 |
| EP | 0014403 A1 | 8/1980 |
| EP | 1542743 A1 | 6/2005 |
| EP | 1670529 A2 | 6/2006 |
| EP | 1525400 B1 | 8/2006 |
| EP | 1559442 B2 | 7/2007 |
| EP | 2113266 A1 | 11/2009 |
| EP | 1807178 B1 | 12/2012 |
| EP | 2463004 B1 | 11/2013 |
| EP | 2739325 A1 | 6/2014 |
| EP | 2421584 B1 | 4/2016 |
| EP | 2282790 B1 | 9/2016 |
| EP | 2704852 B1 | 10/2016 |
| EP | 2500051 B1 | 12/2016 |
| GB | 2495625 A | 4/2013 |
| JP | H01094859 A | 4/1989 |
| JP | H05042220 A | 2/1993 |
| JP | H07163661 A | 6/1995 |
| JP | 2000509620 A | 8/2000 |
| JP | 2007000487 A | 1/2007 |
| JP | 2007044546 A | 2/2007 |
| JP | 2012517275 A | 8/2012 |
| WO | WO-9741904 A1 | 11/1997 |

(56) References Cited

FOREIGN PATENT DOCUMENTS

| WO | WO-16019138 A1 | 2/2016 |
| WO | WO-16123118 A1 | 8/2016 |
| WO | WO-16191747 A1 | 12/2016 |

OTHER PUBLICATIONS

Extended European Search Report for Application No. 21155569.3, dated May 6, 2021, 8 pages.
Japanese Office Action for Application No. 2018561582, dated Mar. 9, 2021, 12 pages including translation.
Australian Office Action for Application No. 2016267688, dated Mar. 5, 2020, 4 pages.
European Office Action for Application No. 17728391.8, dated Mar. 17, 2020, 6 pages.
Chinese Office Action for Application No. 201780046388.0, dated Sep. 27, 2020, 26 pages including translation.
European Office Action for Application No. 16729704.3, dated Oct. 23, 2020, 7 pages.
International Search Report and Written Opinion for Application No. PCT/US2016/034859, dated Oct. 17, 2016, 26 pages.
International Search Report and Written Opinion for Application No. PCT/US2017/034474, dated Aug. 1, 2017, 14 pages.
Invitation to Pay Additional Fees and Partial International Search Report for Application No. PCT/US2016/034859, dated Aug. 19, 2016, 12 pages.
Australia Office Action for Application No. 2017270195, dated Jun. 8, 2021, 4 pages.
Chinese Office Action for Application No. 201780046388.0, dated May 21, 2021, 26 pages including English translation.
Chinese Office Action for Application No. 201680030642.3, dated Jun. 3, 2020, 13 pages.
Japanese Office Action for Application No. 2017-561941, dated Jun. 24, 2020, 23 pages.
Mexican Office Action for Application No. MX/a/2017/014546, dated Mar. 22, 2022, 6 pages including translation.

* cited by examiner

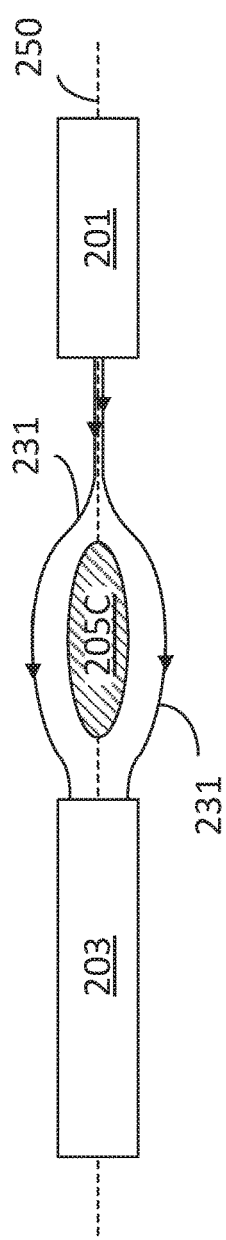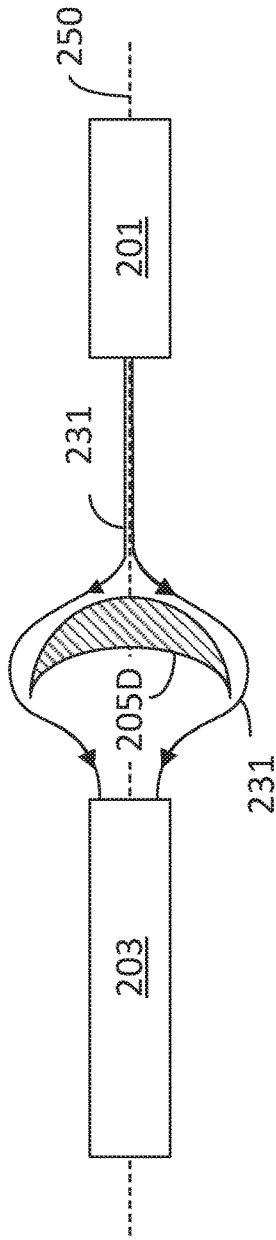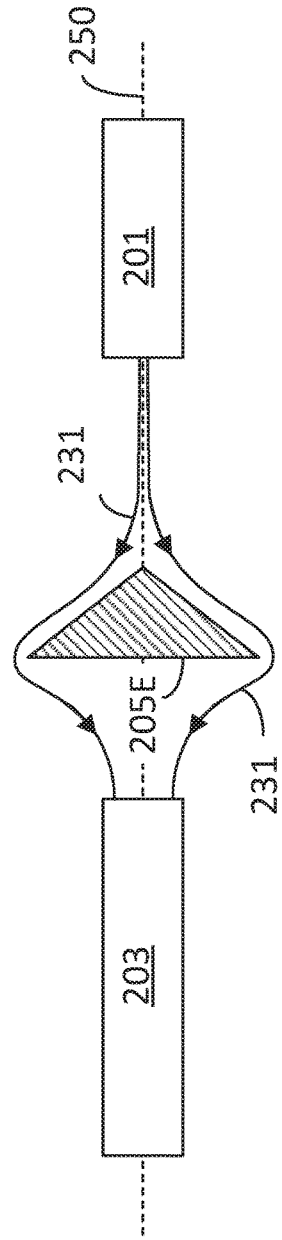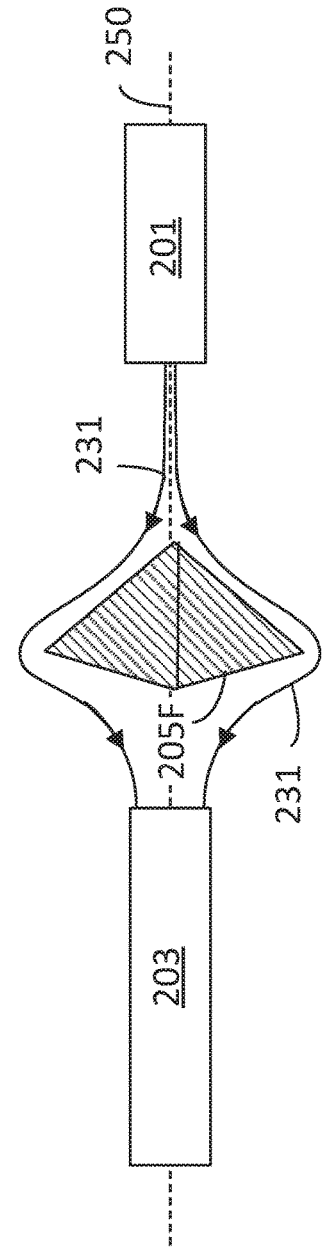

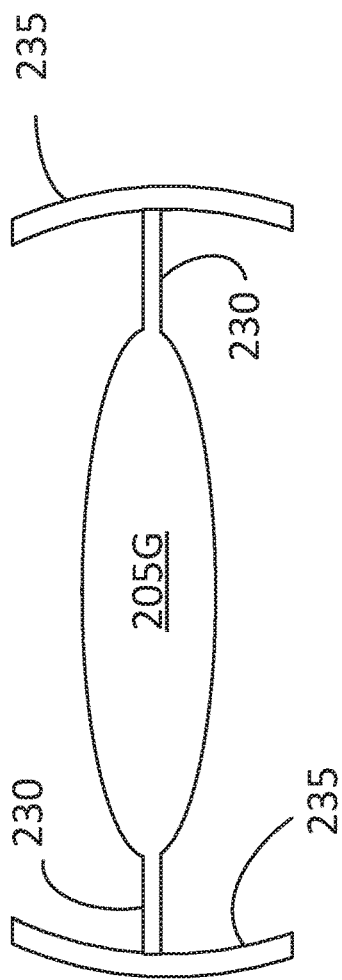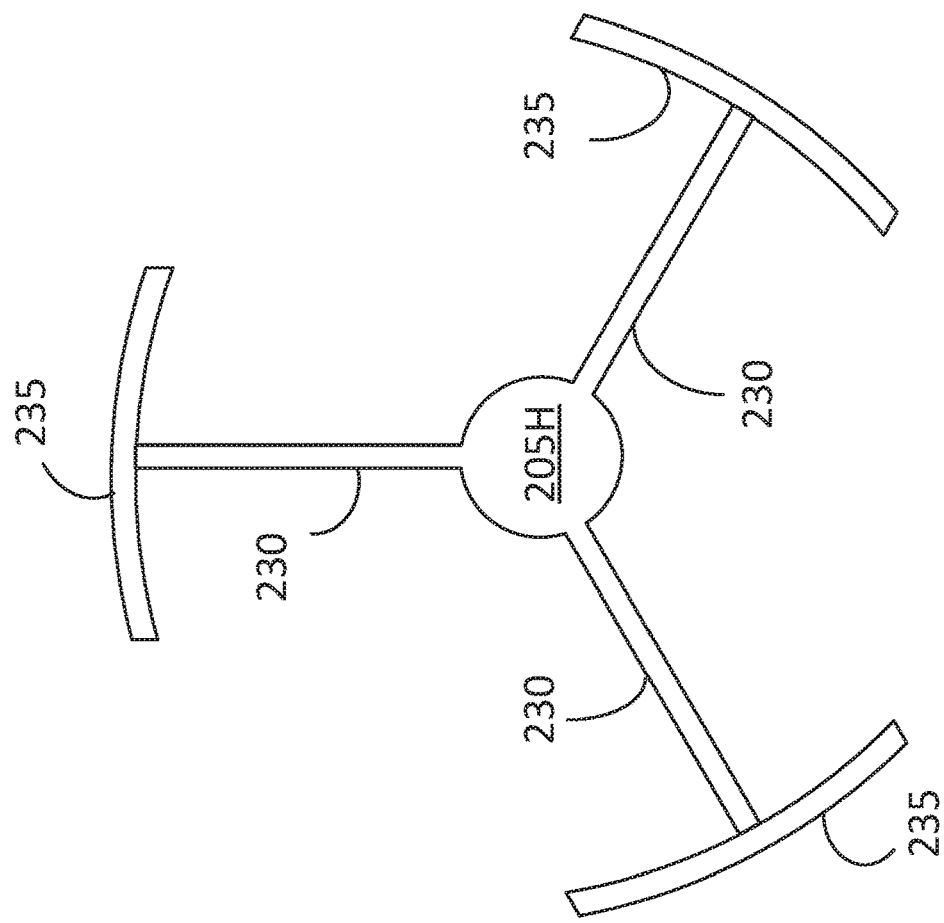
FIG. 2G
FIG. 2H

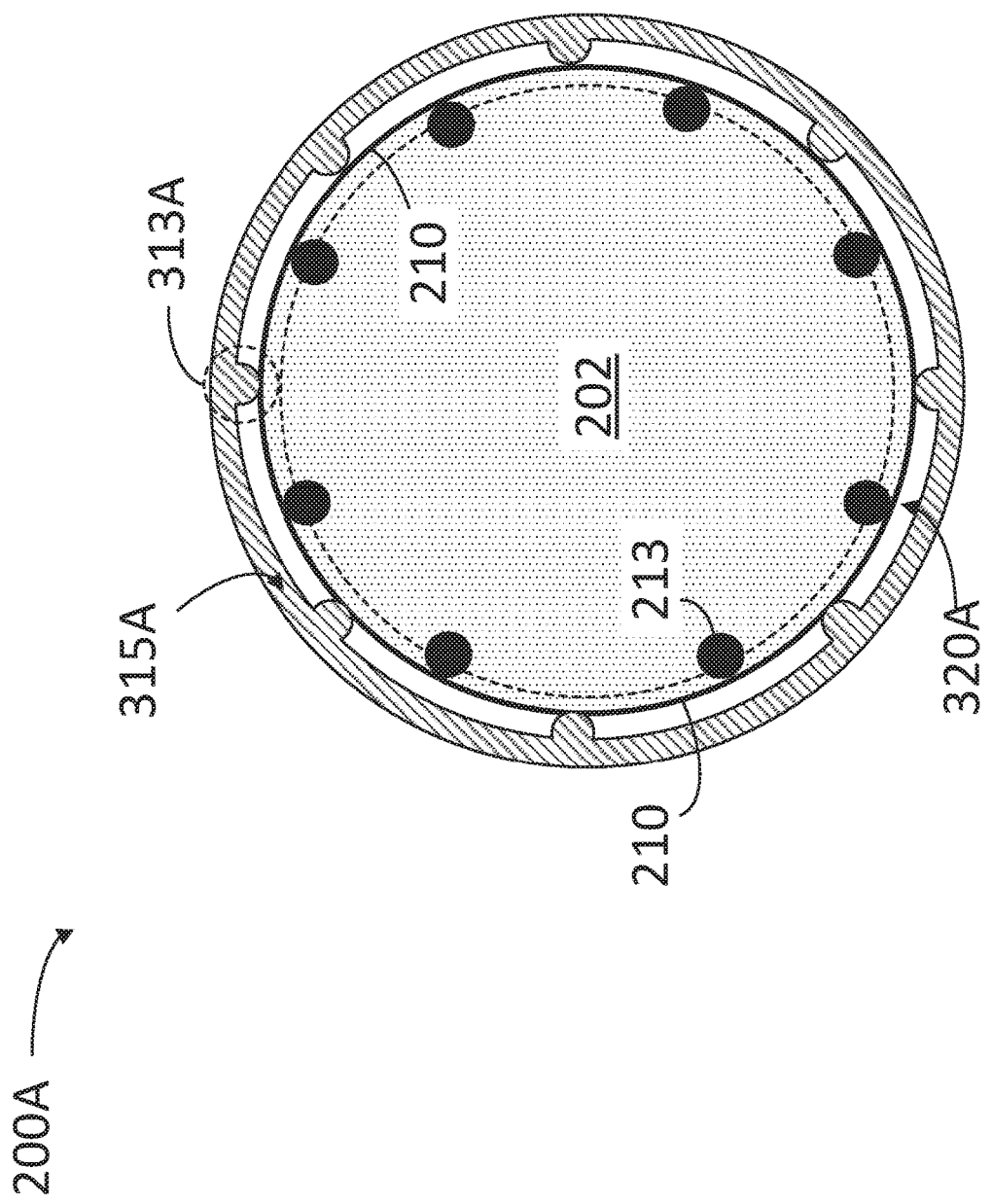

APPARATUS AND METHODS FOR INTRAVENOUS GAS ELIMINATION

CROSS-REFERENCE TO RELATED APPLICATION

This application is the U.S. National Phase under 35 U.S.C. § 371 of International Application No. PCT/US2017/034474, entitled "APPARATUS AND METHODS FOR INTRAVENOUS GAS ELIMINATION," filed May 25, 2017, which claims priority to U.S. application Ser. No. 15/167,914, entitled "APPARATUS AND METHODS FOR INTRAVENOUS GAS ELIMINATION," filed May 27, 2016. The entire contents of these applications are incorporated by reference herein.

BACKGROUND

The present disclosure is generally related to apparatuses and methods for gas elimination in intravenous (IV) delivery systems. More specifically, the present disclosure relates to an apparatus for gas elimination in IV delivery that is independent of the orientation of a fluid line in the IV delivery system.

Many approaches to gas elimination for IV delivery systems include bubble traps making use of the buoyancy of gas bubbles immersed in a liquid. Gas bubbles move up in a liquid container under the influence of gravity, thereby separating gas from liquid. Other approaches to bubble traps include a hydrophilic (i.e., water attractive) membrane to allow liquids to pass through but air to remain trapped on the other side of the membrane.

SUMMARY

Bubble traps based on buoyancy have the drawback that gas accumulates at the top of the bubble trap due to the gas/Liquid density difference and needs to be manually removed by a clinician, thus distracting resources from surgery or therapy and adding the risk of human error, neglect or forgetfulness. Additionally, the orientation of buoyancy-based devices needs to be fixed in space relative to gravity to direct the bubbles to a specified location. When the orientation is not fixed correctly, bubbles may remain in the liquid and can be introduced to the patient. Membrane-based bubble traps which employ a hydrophilic membrane, on the other hand, are not suitable to work with blood products. In fact, the hydrophilic property of the membrane (e.g., pore sizes) can lead to clogging of the membrane by blood cells or blood clots, ultimately blocking the fluid flow altogether.

More generally, some bubble traps do not remove enough bubbles, or are too easily overcome by larger boluses of air, at the flow rates that are common for intravenous (IV) therapy. Accordingly, there is a need for an improved bubble trap or air elimination device which can efficiently remove a wide range of bubble sizes across a wide range of flows for IV fluids including blood products, independent of orientation, and with automatic venting of the gases/air into the atmosphere.

In some embodiments, an apparatus includes a fluid inlet coupling a fluid flow into a liquid chamber. The apparatus also includes a fluid outlet protruding into the liquid chamber and a flow diversion member proximal to the fluid outlet, the flow diversion member configured to block a direct flow between the fluid inlet and the fluid outlet. Moreover, the apparatus may include a membrane separating a portion of the liquid chamber from an outer chamber, and a gas venting valve fluidically coupling the outer chamber with the atmosphere. In some embodiments, the flow diversion member is mechanically supported by at least one strut or elongate member extending along a flow direction into the liquid chamber.

In further embodiments a system includes a container including an intravenous liquid, a mechanism to provide a pressure to move the intravenous liquid through a fluid line to a patient, a fluid line, and a gas elimination apparatus fluidically coupled with the fluid line and configured to remove gas bubbles from the intravenous liquid. The gas elimination apparatus includes a flow diversion member configured to block a direct flow between a fluid inlet and a fluid outlet, the flow diversion member supported by at least one strut or elongate member extending from the fluid outlet to the flow diversion member. The gas elimination apparatus also includes a membrane separating a portion of the fluid chamber from an outer chamber, and a gas venting valve fluidically coupling the outer chamber and the atmosphere.

In yet other embodiments, an apparatus includes a fluid inlet coupling a fluid flow into a liquid chamber, and a fluid outlet protruding into the liquid chamber. The apparatus includes a flow diversion member proximal to the fluid outlet, the flow diversion member configured to divert a flow between the fluid inlet and the fluid outlet in a radial direction away from the fluid outlet, and a membrane separating a the liquid chamber from an outer chamber and forming an inner surface of the outer chamber, the membrane configured to allow a gas to pass through from the liquid chamber to the outer chamber. Further, the apparatus includes a gas venting valve fluidically coupling the outer chamber with the atmosphere, wherein the flow diversion member is mechanically supported by at least one elongate member extending from the fluid inlet along a flow direction into the liquid chamber.

In some embodiments, a method includes forming a liquid chamber having a fluid inlet and a fluid outlet, and forming an outer chamber having an inner surface including a membrane separating the liquid chamber from the outer chamber. The method further includes forming a relief valve in the outer chamber, the relief gas configured to release a gas stored in the outer chamber into the atmosphere, and disposing a flow diversion member proximal to the fluid outlet to divert a flow between the fluid outlet in a radial direction away from the fluid outlet. The method also includes disposing a sheet comprising an absorbing element in the outer chamber to absorb a fluid condensate in the outer chamber.

BRIEF DESCRIPTION OF THE DRAWINGS

FIGS. 2C-F illustrate cross sectional views of a flow diversion member in a gas elimination apparatus for use in an intravenous system, according to some embodiments.

FIGS. 2G-H illustrate front views of a flow diversion member and the struts connecting the flow diversion member to a wall of a gas elimination apparatus for use in an intravenous system, according to some embodiments.

FIG. 3A illustrates a cross-sectional view of a gas elimination apparatus for use in an IV delivery system, according to some embodiments.

In the figures, elements having the same or similar reference numeral have the same or similar functionality or configuration, unless expressly stated otherwise.

DETAILED DESCRIPTION

During IV delivery of liquids (e.g., crystalloids, colloids, blood products, drugs) to patients, a risk exists wherein gas bubbles or gas boluses may be inadvertently delivered into the body through the delivery system. Because the amount of air that can be tolerated by an individual patient may vary or be uncertain, caregivers make every effort to remove all gases and even small gas bubbles during the setup (priming) of the delivery system. Unfortunate errors can occur during this process, leaving some air/gas remaining in the delivery lines which should ideally be removed. Furthermore, once a system is primed, there exist additional mechanisms for air/gas to be introduced into the tubing leading to the patient. These mechanisms include hanging of new IV bags, introduction of bolus injections through access ports, and warming of the IV fluid, which inherently leads to out-gassing. The latter occurs because the solubility of a gas in a liquid is dependent upon temperature. IV bags are typically introduced either near freezing temperatures (e.g., blood products) or at room temperature (e.g., most other fluids like colloids and crystalloids). When these fluids are warmed from freezing or room temperature up to a higher temperature near body temperature (e.g., 37-41° C.), gases come out of the liquid in the form of bubbles which are desirably removed to avoid delivering them to the patient. In most disposable IV sets, this is achieved using a bubble "trap" of some sort.

The present disclosure includes a gas elimination device, which is orientation independent, works with many IV fluids including blood products, and automatically vents trapped gases to the ambient environment. Embodiments of a gas elimination apparatus as disclosed herein may advantageously be placed just downstream of a fluid warming device where bubbles are formed by out-gassing, or may be placed at other locations in an IV delivery system to remove air/gas. The present disclosure may include additional features such as the ability to stop flow using a valve (e.g., stopcock) and/or the ability to introduce bolus drug injections on the upstream side to allow clinicians peace of mind that any air/gas they inadvertently introduce during an injection into the system will be removed prior to the liquid reaching the patient.

Gas elimination devices for use in intravenous delivery systems as disclosed herein may use the lower density of gases versus liquids to allow bubbles to migrate to a region where they can be automatically removed, and some embodiments employ membranes exploiting differences between how gases and liquids interact with surfaces of a given energy state. For example, some embodiments employ a hydrophobic (i.e., water averse) membrane to allow air/gas to escape into a room atmosphere, but liquid to remain in the system.

Figure 1:
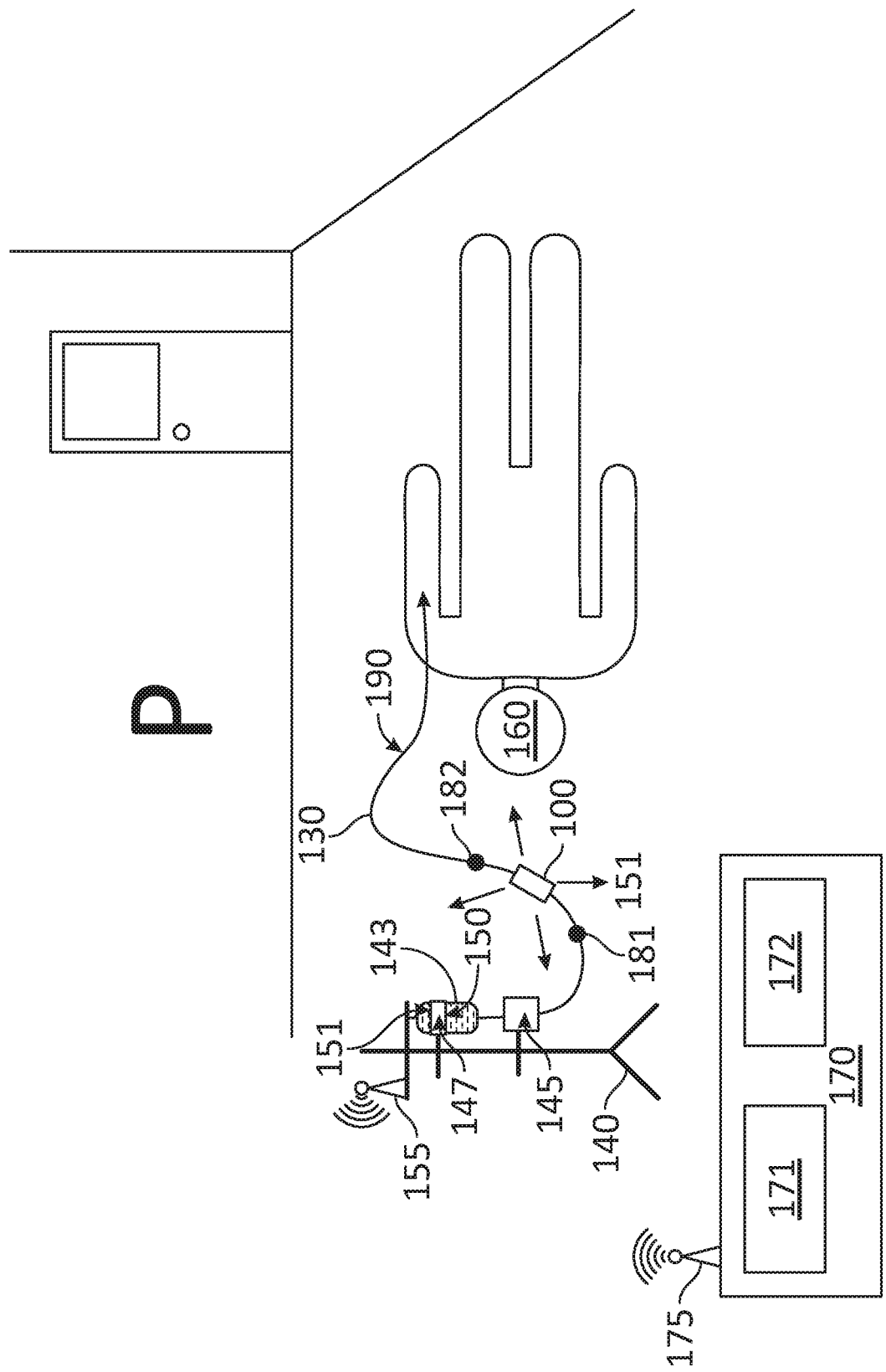
FIG. 1 illustrates an intravenous delivery system, according to some embodiments.

FIG. 1 illustrates an IV delivery system according to some embodiments. The IV delivery system includes a frame 140 supporting a container 143 having an intravenous liquid 150. In some embodiments, intravenous liquid 150 includes a gas that may be dissolved, may be in the form of gas bubbles 151, may form a gas phase above a liquid surface, or comprise any combination of these forms. Gas in gas bubbles 151 may be air, nitrogen, oxygen, or any other gas susceptible of being dissolved in intravenous liquid 150. Intravenous liquid 150 may be any liquid suitable for intravenous delivery. Common intravenous liquids include crystalloids (e.g., saline, Lactated Ringers, glucose, dextrose), colloids (e.g., hydroxyethyl starch, gelatin), liquid medications, buffer solutions, and blood products (e.g., packed red blood cells, plasma, clotting factors) or blood substitutes (e.g., artificial blood) that are desired to be injected intravenously to a patient 160. A fluid line 130 carries intravenous liquid 150 from container 143 to patient 160. In some embodiments, intravenous liquid 150 moves through fluid line 130 by a pressure differential created by gravity. Accordingly, in some embodiments container 143 is disposed on frame 140 at a higher elevation relative to the patient. In some embodiments, a pump 145 creates the pressure differential to move liquid 150 through fluid line 130.

Some embodiments of an IV delivery system consistent with the present disclosure include a thermostat 147 to adjust a temperature of intravenous liquid 150 in container 143. The IV delivery system includes a gas elimination apparatus 100 fluidically coupled with fluid line 130. Gas elimination apparatus 100 is configured to remove gas bubbles 151 from liquid 150. In some embodiments, gas elimination apparatus 100 is configured to automatically remove gas bubbles 151 from intravenous liquid 150 with minimal intervention from a healthcare professional. Further, according to some embodiments, gas elimination apparatus 100 is configured to remove gas bubbles 151 from liquid 150 regardless of its orientation relative to gravity. In some embodiments, gas bubbles 151 are removed from intravenous liquid 150 in fluid line 130 and released to the room at atmospheric pressure P.

In some embodiments, the operation of an IV delivery system as depicted in FIG. 1 may be controlled wirelessly by a remote controller 170 located, for example, at a nurse station. The wireless communication may be performed by an antenna 175 on the controller side and an antenna 155 on frame 140. Controller 170 includes a processor 171 and a memory 172. Memory 172 may include commands and instructions, which when executed by processor 171, cause controller 170 to perform at least partially some of the steps included in methods consistent with the present disclosure. Further according to some embodiments, a first bubble sensor 181 may be placed upstream from gas elimination apparatus 100, and a second bubble sensor 182 may be placed downstream from gas elimination apparatus 100. Bubble sensors 181 and 182 may include any type of sensing devices, including optical sensors, a video camera and a laser, ultrasound sensors or other electrical types of sensing devices, such as a capacitance measuring circuit, or the like.

In that regard, at least one of bubble sensors 181 and 182 may provide information about a number of bubbles per cross-sectional area, per unit time, flowing through fluid line 130, and their approximate diameter. Furthermore, bubble sensors 181 and 182 may wirelessly communicate with antenna 155 and with controller 170, to receive instructions from and provide data to, controller 170.

Controller 170, antenna 155, and bubble sensors 181 and 182 may communicate via a Bluetooth, Wi-Fi, or any other radio-frequency protocol. Accordingly, controller 170 may be configured to process a reading from bubble sensors 181 and 182 and determine a bubble elimination rate for gas elimination apparatus 100. Based on the bubble elimination rate, controller 170 may provide commands to pump 145 and other devices within frame 140 to increase the bubble elimination rate. Furthermore, controller 170 may provide an alarm to a centralized system when a bubble count in sensor 182 becomes higher than a first threshold, or when the bubble elimination rate becomes lower than a second threshold. In some embodiments, controller 170 may also provide commands to thermostat 147 to regulate the temperature of intravenous liquid 150 based on the bubble counts provided by at least one of sensors 181 and 182. A valve 190 in fluid line 130 may be operated to allow intravenous liquid 150 to flow into patient 160 when bubble sensor 182 detects a bubble content lower than a predetermined threshold. In some embodiments, valve 190 may be closed by controller 170 when an alarm is issued as described above.

Figure 2A:
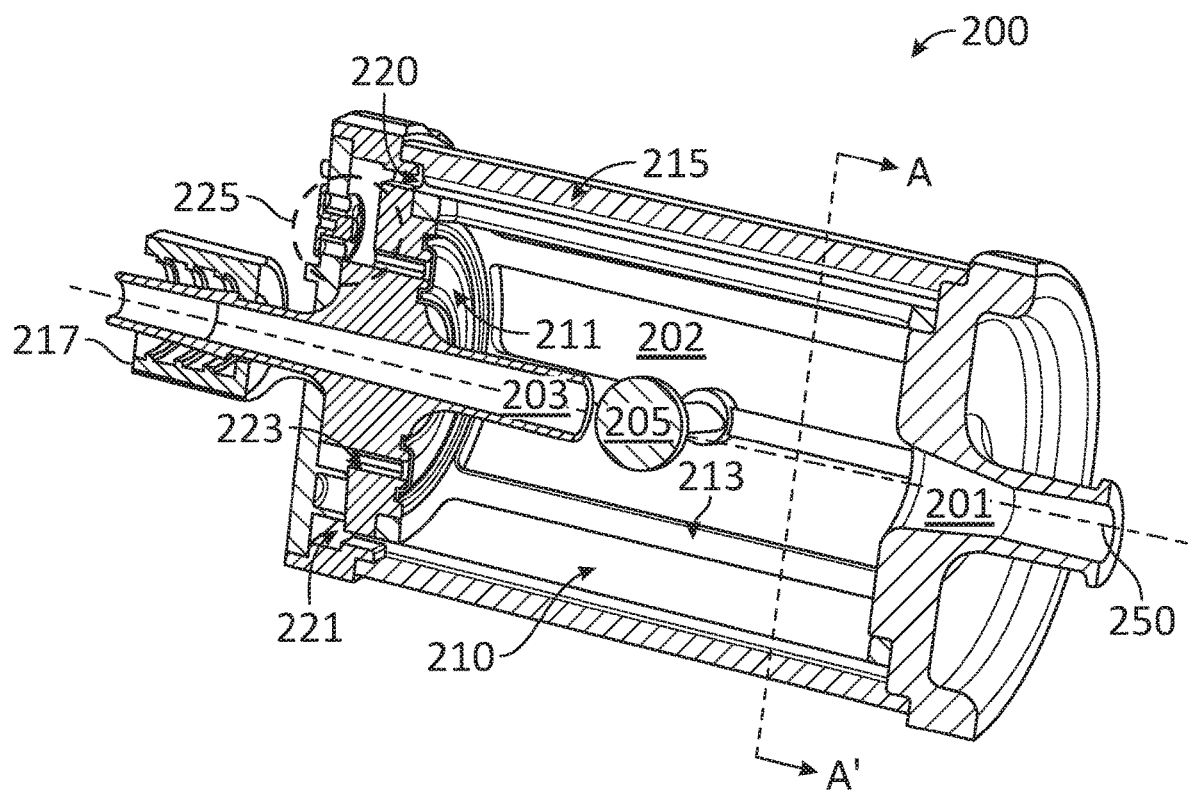
FIG. 2A illustrates a gas elimination apparatus for use in an intravenous system, according to some embodiments.

FIG. 2A illustrates a gas elimination apparatus 200 for use in an intravenous system, according to some embodiments. Gas elimination apparatus 200 includes a fluid inlet 201 coupling a fluid flow into a liquid chamber 202. A fluid outlet 203 protrudes into liquid chamber 202 to collect and deliver the bubble-deficient fluid to fluid line 130, which is coupled to apparatus 200 through a connector 217. A flow diversion member 205 proximal to fluid outlet 203 is configured to block a direct fluid flow between fluid inlet 201 and fluid outlet 203. Accordingly, the fluid flow that is transferred out through fluid outlet 203 has spent some time in liquid chamber 202 before exiting, allowing bubbles 151 to migrate to an outer chamber 220 through a first membrane 210 and a second membrane 211. A wall 215 provides support to membranes 210 and 211, and also to flow diversion member 205. In some embodiments, a support cage 213 may provide further structural support to membranes 210 and 211. This may be especially beneficial when membranes 210 and 211 include a sheet membrane, which may be flexible or soft. Membranes 210 and 211 cover a portion of the interior surface of liquid chamber 202, and separate liquid chamber 202 from outer chamber 220. Accordingly, when intravenous liquid 150 comes in contact with membranes 210 and 211, gas bubbles 151 contained in the fluid are allowed to pass through the membrane pores, while water and other solvents or elements in intravenous liquid 150 are contained by membranes 210 and 211 within interior chamber 202.

Gas elimination apparatus 200 includes a gas venting valve 225 fluidically coupling outer chamber 220 with the atmosphere. Outer chamber 220 is fluidically coupled with valve chamber 221. A conduit 223 transports gas from gas bubbles 151 going through membrane 211 to valve chamber 221. Accordingly, when outer chamber 220 is filled with air or gas from bubbles 151, pressure inside outer chamber 220 builds up until valve 225 is opened and the gas flows out into the atmosphere. Outer chamber 220 and membranes 210 and 211 may be transparent or semi-transparent, thus allowing at least a partial view of the interior to a healthcare professional. Alternatively, outer chamber 220 and membranes 210 and 211 may be opaque. Membranes 210 and 211 may be formed of polymeric materials such as polytetrafluoroethylene (PTFE), and may have a pore size which ranges from 0.1 to a few microns ($10^{-6}$ m). The thickness of membranes 210 and 211 may be in the range of 100-200 microns. In some embodiments, the water breakthrough pressure may be approximately 2-3 bar. The gas flow venting capability of membranes 210 and 211 is preferably in the range of 400-700 milliliters per minute, per square cm (ml/min/cm$^2$) but may be higher or lower. Membranes 210 and 211 may comprise thin, flexible, compliant forms or may be solid or semi-solid, rigid forms. Similarly, membranes 210 and 211 may take the form of sheets or may be formed into specific self-supporting shapes in a manufacturing step. It should be understood however, that any membrane with appropriately hydrophobic properties may be used, consistent with the scope of the disclosure.

More specifically, membranes 210 and 211 may include a hydrophobic membrane ("water averting"). In some embodiments, membranes 210 and 211 may include a hemophobic ("blood averting") membrane, an oleophobic ("oil averting") membrane, or any combination of the above. Accordingly, membranes 210 and 211 may be used with any IV fluids and may be resistant to wetting with both high and low surface tension fluids as well as blood and blood products. In some embodiments, membranes 210 and 211 are constructed of polyvinylidene fluoride (PVDF) and are capable of passing air or other gases in both directions.

The form factor of gas elimination apparatus 200 allows it to eliminate gas bubbles 151 from intravenous liquid 150 in any orientation relative to gravity. In some embodiments, liquid chamber 202 is a cylindrical chamber having a longitudinal axis 250. Membranes 210 and 211 form the wall, ceiling, and floor of liquid chamber 202. As gas bubbles 151 or gas 'slugs' enter liquid chamber 202, they encounter at least one of membranes 210 and 211 before ever entering fluid outlet 203, regardless of the orientation of axis 250 relative to gravity. For example, when the device is oriented with longitudinal axis 250 perpendicular to the direction of gravity (horizontal, cf. FIG. 1), gas bubbles 151 rise to the apex of the circular cross section of the cylinder, reaching membrane 210 and filtering through to outer chamber 220. When the device is oriented with longitudinal axis 250 parallel to the direction of gravity (vertical, cf. FIG. 1), gas bubbles 151 rise to the ceiling or floor to encounter membrane 211. When bubbles or gases reach membranes 210 and 211, they transit through from interior chamber 202 into outer chamber 220. In some embodiments, outer chamber 220 prevents introduction of gases back into intravenous liquid 150 from the ambient, which can occur when the partial pressure differential across the membrane is directed towards interior chamber 202. As such, gases that are removed from interior chamber 202 into outer chamber 220 are automatically vented through the one or more valves 225 or additional membranes (e.g., umbrella type). In some embodiments, valves 225 may be one-way operating valves that allow gases to escape into the atmosphere but not to enter back into gas elimination apparatus 200.

Dimensions of gas elimination apparatus 200 in embodiments consistent with the present disclosure allow gas bubbles 151 of expected sizes greater than a minimum value to reach membranes 210 and 211 in less than the transit time it takes intravenous liquid 150 to travel from fluid inlet 201 to fluid outlet 203. For example, the length of the liquid chamber 202 may be approximately 30 mm (along longitudinal axis 250) and the diameter of internal chamber 202 may be approximately 20 mm, With such dimensions, sub-microliter bubbles (<1 mm in diameter) may be transferred to outer chamber 220 before traversing the length of liquid chamber 202 due to their buoyancy. In some embodiments, the length of liquid chamber 202 may be up to 50 mm, or more, while the diameter of liquid chamber 202 may be somewhere between 10 mm to 20 mmm as desired.

Additional non-cylindrical shapes of liquid chamber 202 may be consistent with an orientation-independent gas elimination apparatus as disclosed herein. For example, triangular, rectangular, pentagonal, hexagonal, heptagonal, octagonal, and higher face-number shaped liquid chambers may perform similarly. The cylindrical shape of liquid chamber 202 is well suited for fabrication and handling due to its symmetric, continuous nature.

Figure 2B:
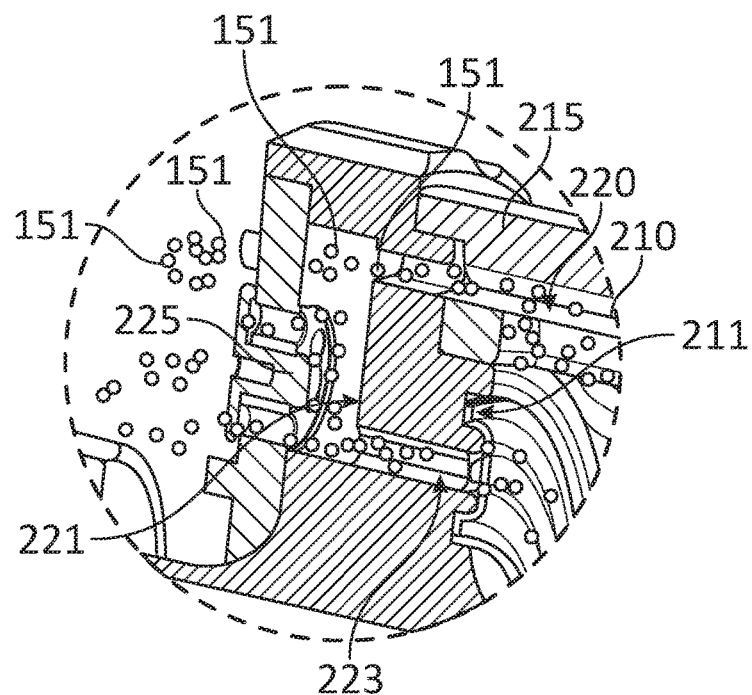
FIG. 2B illustrates a detail of a gas elimination apparatus for use in an intravenous system, according to some embodiments.

FIG. 2B illustrates a detail of gas elimination apparatus 200, according to some embodiments. Gas bubbles 151 transit through membrane 210 and from outer chamber 220 into valve chamber 221. Also, some gas bubbles 151 transit through membrane 211 and conduit 223 into valve chamber 221. Accordingly, gas bubbles 151 build up a pressure inside valve chamber 221 such that eventually the pressure becomes about the same as or somewhat greater than room pressure P (cf. FIG. 1). At this point, valve 225 automatically opens, releasing the excess pressure in the form of the gas inside gas bubbles 151.

FIGS. 2C-F illustrate cross sectional views of flow diversion members 205C-F in gas elimination apparatus 200 for use in an intravenous system, according to some embodiments. Flow diversion members 205C-F prevent or restrict bubbles 151 from traveling in straight lines directly from fluid inlet 201 to fluid outlet 203. This may be desirable during operation in an orientation where longitudinal axis 250 is parallel to the direction of gravity (vertical, cf. FIG. 1), however, even during operation where longitudinal axis 250 is perpendicular to the direction of gravity (horizontal, cf. FIG. 1), diversion members 205C-F induce bubbles 151 to substantially follow the plurality of flow streamlines 231 along a curved path from fluid inlet 201 to fluid outlet 203. Flow diversion members 205C-F force bubbles 151 or gas slugs to migrate (e.g., through diverted flow streamlines 231 and buoyancy) towards membranes 210 and 211 prior to any chance to make multiple turns and reach fluid outlet 203. Flow diversion members 205C-F substantially or completely block fluid outlet 203 when viewed from fluid inlet 201 along axis 250. In some embodiments, flow diversion members 205C-F allow a blood component other than a gas bubble to reach fluid outlet 203, and thereby stay in the flow stream. For example, a blood component as disclosed herein may include any one of a red blood cell, or any undissolved solid in the blood stream. Accordingly, flow streamlines 231 emanating from fluid inlet 201 reach fluid outlet 203 along a path that deviates from a straight line path. Flow diversion members 205C-F may present a hydrodynamic form factor to the flow of the intravenous liquid 150 or may present a non-hydrodynamic form factor such as a stagnation plane. In embodiments consistent with the present disclosure, the surface of flow diversion members 205C-F presented to the incoming flow of intravenous liquid 150 (the right hand side of flow diversion members 205C-F in FIGS. 2C-F) may be spherical or dome shaped to smoothly divert the liquid flow outwards and away from fluid outlet 203. Examples of non-spherical or semi-spherical (e.g., having one or more features similar to a sphere) shapes of flow diversion member 205 consistent with the gas elimination apparatus as disclosed herein include flow diversion member 205C with ellipsoidal shape, flow diversion member 205D with a mushroom or umbrella shape, or pyramidal shapes. FIG. 2E illustrates flow diversion member 205E that is conical, and FIG. 2F illustrates flow diversion member 205F with a pyramidal shape. One of ordinary skill will recognize that the shape of flow diversion member 205 may be any desired shape, such as a disc, or the like. Additionally, the expanse (cross-sectional area with respect to axis 205) of flow diversion member 205 may beneficially extend beyond the diameter of fluid outlet 203 to force bubbles 151 further away from the outlet and direct them closer to membranes 210 and 211 (e.g., flow diversion members 205D-F).

FIGS. 2G-H illustrate front views of flow diversion members 205G-H and struts 230 connecting flow diversion member 205G-H to wall 215 of gas elimination apparatus 200 according to some embodiments. Struts 230 in flow diversion members 205G-H may have hydrodynamic shapes to avoid additional pressure loss to the liquid as it passes through gas elimination apparatus 200. For example, struts 230 may be thin hydrofoils presenting a low and smooth angle of attack to the incoming fluid. As illustrated in FIGS. 2G-H, struts 230 may be attached to wall 215 through supports 235. In some embodiments, the material for flow diversion members 205G-H, struts 230, and supports 235 may be the same as the material for support cage 213 and wall 215 in gas elimination apparatus 200.

FIG. 3A illustrates a cross-sectional view of gas elimination apparatus 200A for use in an IV delivery system, according to some embodiments. The cross-sectional view illustrated in FIG. 3A is taken along segment A-A' in FIG. 2A. Gas elimination apparatus 200A includes wall 315A having protrusions 313A contacting wall 215, thus providing structural support to membrane 210 and to outer chamber 320A. Protrusions 313A are formed from wall 315A and may contact membrane 210 at points alternating with features of support cage 213. Accordingly, protrusions 313A may be parallel to longitudinal axis 250. Outer chamber 320A is analogous to outer chamber 220 (cf. FIG. 2A). Accordingly, the risk of collapse when there is low gas pressure in outer chamber 320A is substantially reduced.

Figure 3B:
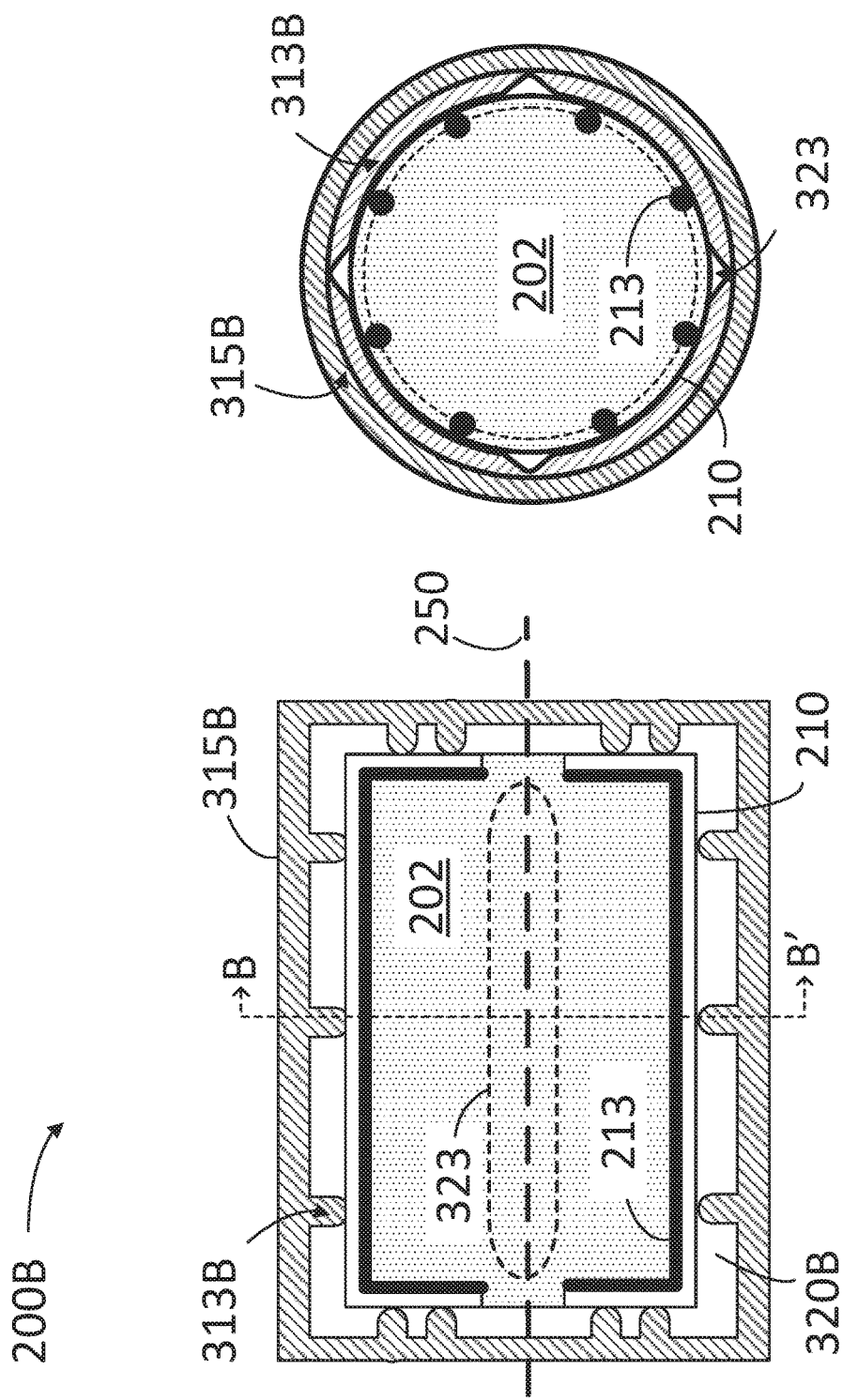
FIG. 3B illustrates a longitudinal and a sagittal cross-sectional view of a gas elimination apparatus for use in an IV delivery system, according to some embodiments.

FIG. 3B illustrates a longitudinal and a sagittal cross-sectional view of gas elimination apparatus 200B for use in an IV delivery system, according to some embodiments. The sagittal cross-sectional view in FIG. 3B corresponds to segment B-B' in the longitudinal cross-sectional view. Gas elimination apparatus 200B includes wall 315B having protrusions 313B contacting membrane 210 and providing structural support to outer chamber 320B. Support cage 213 supports membrane 210 as illustrated in gas elimination apparatus 200A. Outer chamber 320B is analogous to outer chamber 220 (cf. FIG. 2A). In some embodiments, protrusions 313B are perpendicular to longitudinal axis 250.

In some embodiments, protrusions 313B include depressions 323 intersecting the protrusions to provide a flow continuity to outer chamber 320B.

Figure 3C:
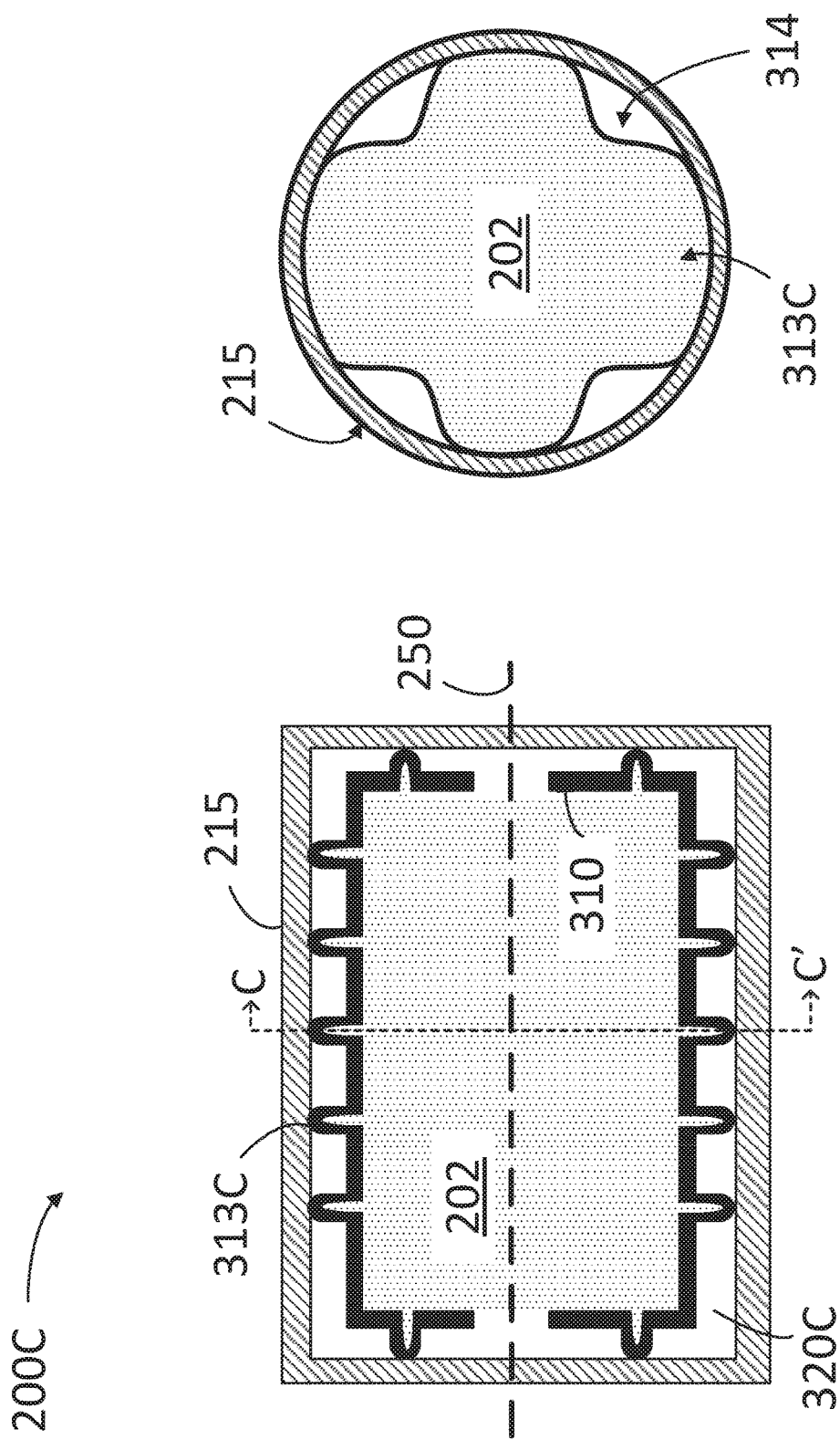
FIG. 3C illustrates a longitudinal and a sagittal cross-sectional view of a gas elimination apparatus for use in an IV delivery system, according to some embodiments.
Figure 4A:
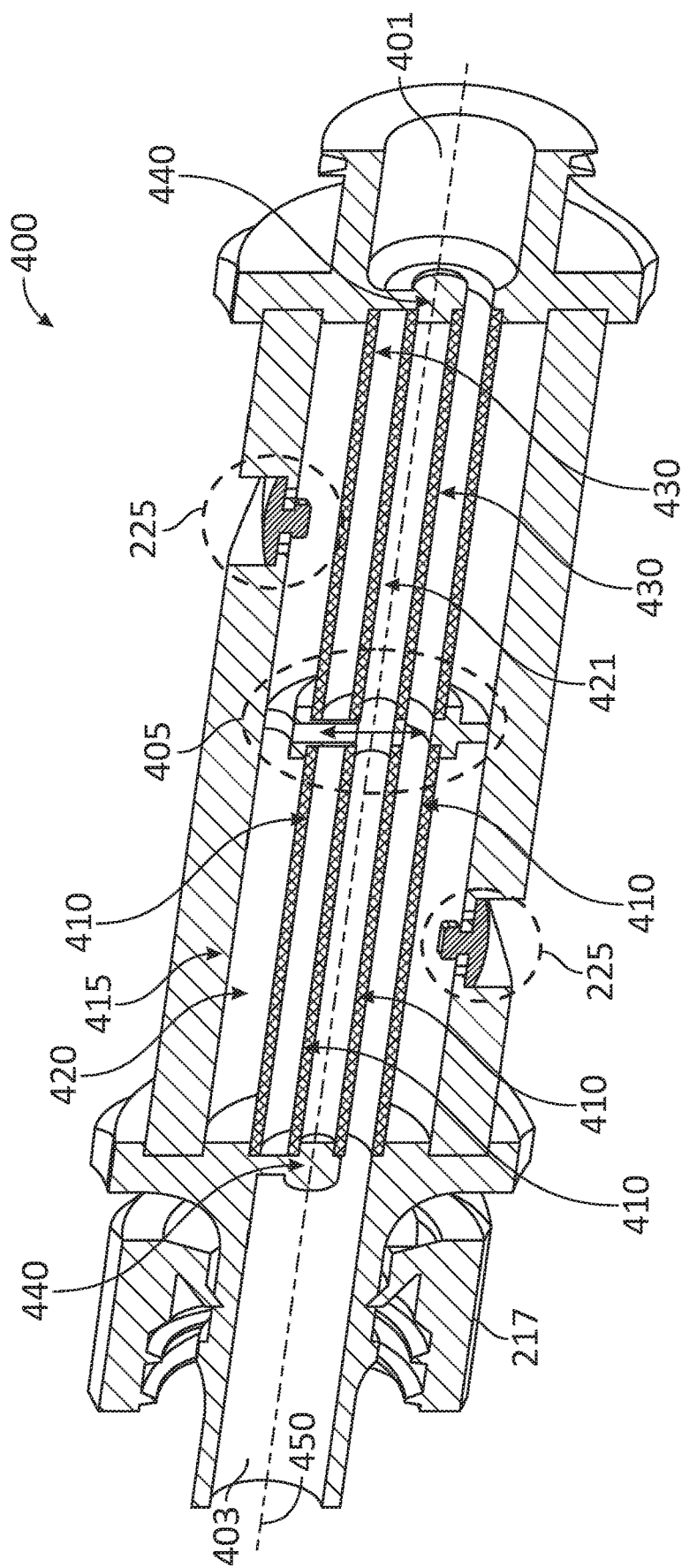
FIG. 4A illustrates a perspective of a gas elimination apparatus for use in an IV delivery system, according to some embodiments.

FIG. 3C illustrates a longitudinal and a sagittal cross-sectional view of gas elimination apparatus 200C for use in an IV delivery system, according to some embodiments. Gas elimination apparatus 200C includes a rigid membrane 310 having protrusions 313C forming outer chamber 320C. The sagittal cross-sectional view illustrated in FIG. 3C is taken along segment C-C' of the longitudinal cross-sectional view, and shows protrusions 313C in more detail. Protrusions 313C are formed in a plane substantially perpendicular to axis 250 and include notches 314 or gaps to allow for air/gas bubbles 151 to pass through, thereby forming a fluidically connected outer chamber 320C, FIG. 4A illustrates a perspective of a gas elimination apparatus 400 for use in an IV delivery system, according to some embodiments. Gas elimination apparatus 400 comprises a fluid inlet 401 coupling a fluid flow into a liquid conduit 430. Liquid conduit 430 is concentric with a hollow chamber 421 along a longitudinal axis 450, wherein hollow chamber 421 is separated from liquid conduit 430 by a membrane 410. Gas elimination apparatus 400 also includes a fluid outlet 403 fluidically coupled with liquid conduit 430, an outer chamber 420 concentric with liquid conduit 430 and separated from liquid conduit 430 by a membrane 410. In some embodiments, gas elimination apparatus 400 includes a center hub 405 fluidically coupling hollow chamber 421 and outer chamber 420. Further, some embodiments include gas venting valve 225 fluidically coupling outer chamber 420 and the atmosphere. In some embodiments, gas elimination apparatus 400 further includes supports 440 on either end of hollow chamber 421. Supports 440 block or restrict the liquid flow through hollow chamber 421, so that only or mostly gas from gas bubbles 151 accumulates in hollow chamber 421.

Figure 4B:
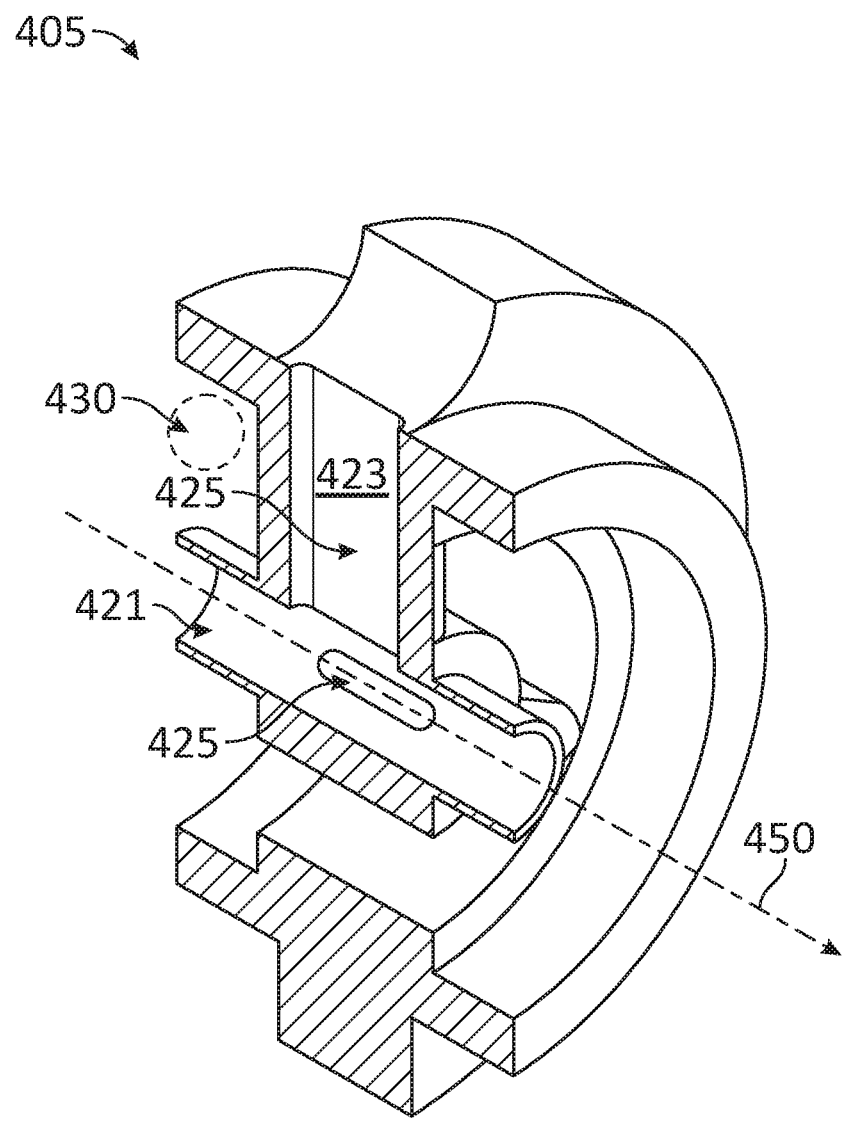
FIG. 4B illustrates a center hub for a gas elimination apparatus for use in an IV delivery system, according to some embodiments.

FIG. 4B illustrates center hub 405 for gas elimination apparatus 400 for use in an IV delivery system, according to some embodiments. Center hub 405 is supported on wall 415 of outer chamber 420 through radial spokes 423. Radial spokes 423 may be hollow and have a conduit 425 fluidically coupling hollow chamber 420 with the outer chamber.

Figure 4C:
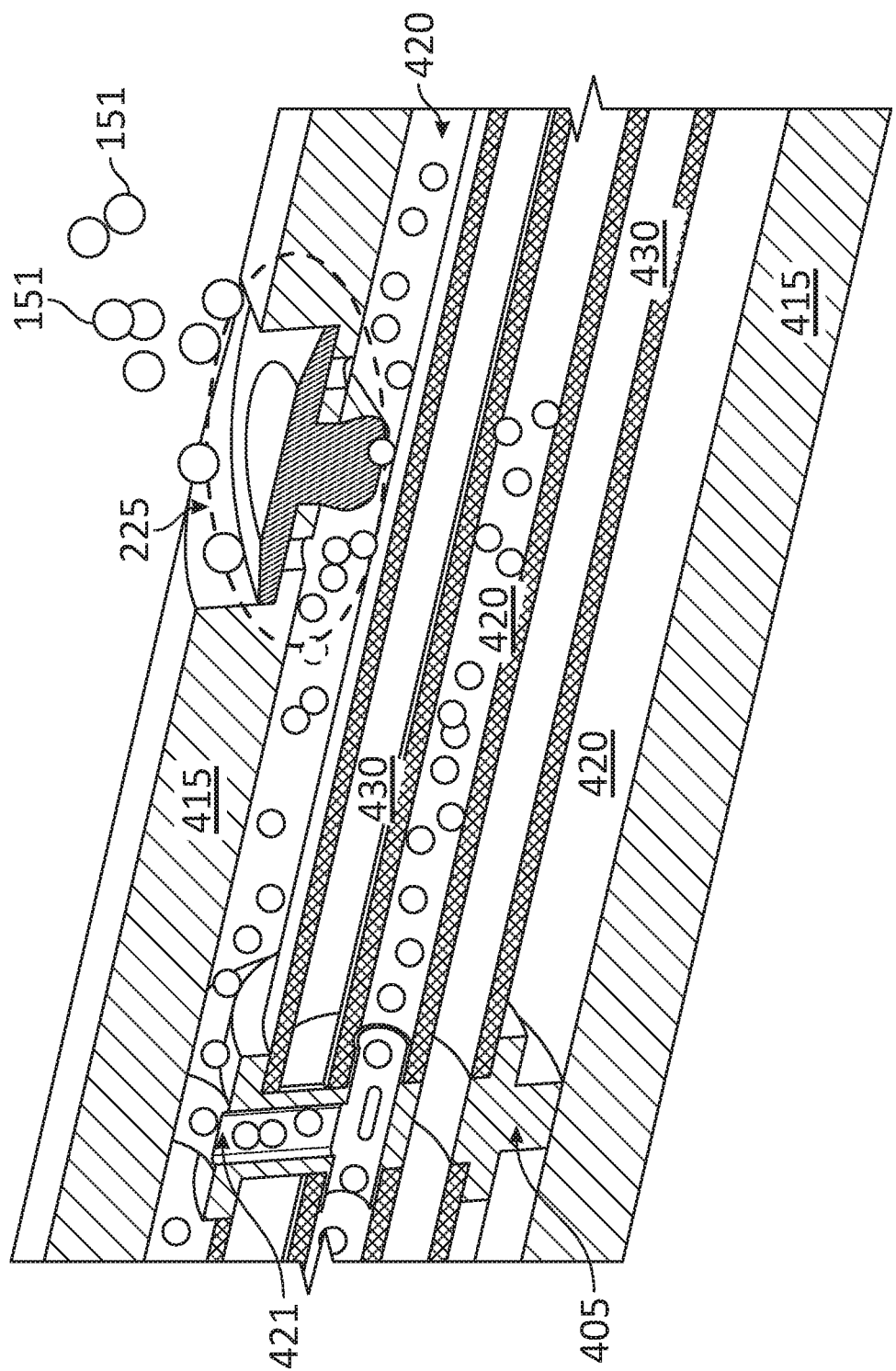
FIG. 4C illustrates a detail of a gas elimination apparatus for use in an IV delivery system, according to some embodiments.

FIG. 4C illustrates a detail of gas elimination apparatus 400 for use in an IV delivery system, according to some embodiments. Gas bubbles 151 transit through membrane 410 into hollow chamber 421 and into outer chamber 420. The gas in hollow chamber 421 is transferred into outer chamber 420 through conduits 425 in spokes 423 of hub 405. Once enough gas pressure builds up in outer chamber 420, valve 225 opens automatically, releasing the gas in gas bubbles 151 into the atmosphere.

Figure 5:
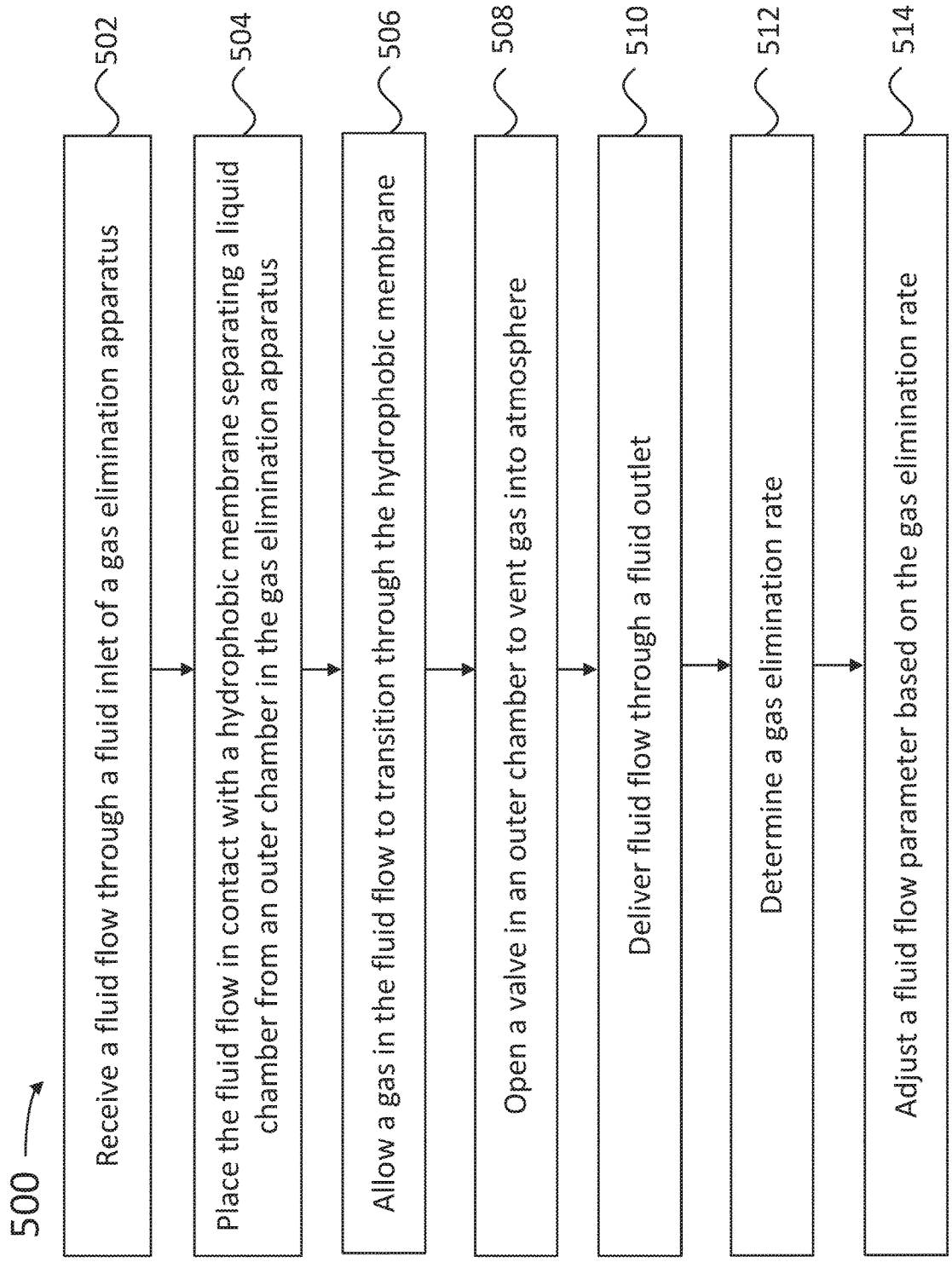
FIG. 5 illustrates a flowchart in a method for delivering a fluid medication with an IV delivery system, according to some embodiments.

FIG. 5 illustrates a flowchart in a method 500 for delivering an intravenous liquid with an intravenous system, according to some embodiments. Methods consistent with method 500 may include using a gas elimination apparatus as disclosed herein, having at least one membrane (e.g., gas elimination apparatus 100, 200, 200A-C, and 400, and membranes 210, 211, and 410, cf. FIGS. 1, 2A-H, 3A-C and 4A, respectively). Further according to some embodiments, methods consistent with the present disclosure may include an IV delivery system as disclosed herein. The IV delivery system may include a frame, a fluid container, a pump, a thermostat, a fluid line, an antenna, at least a bubble sensor, and a valve as disclosed herein (e.g., frame 140, fluid container 143, pump 145, fluid line 130, antenna 155, bubble sensors 181 and 182, and valve 190, cf. FIG. 1).

Methods consistent with method 500 may include at least one step in method 500 performed by a controller including a memory and a processor (e.g., controller 170, processor 171, and memory 172, cf. FIG. 1). The memory storing commands, which when executed by a processor cause the controller to perform at least one step in method 500. Further according to some embodiments, methods consistent with method 500 may include at least one, but not all, of the steps illustrated in FIG. 5. Moreover, in some embodiments a method as disclosed herein may include steps in method 500 performed in a different sequence than that illustrated in FIG. 5. For example, in some embodiments at least two or more of the steps in method 500 may be performed overlapping in time, or even simultaneously, or quasi-simultaneously.

Step 502 includes receiving a fluid flow through the fluid inlet of the gas elimination apparatus. In some embodiments step 502 includes sending commands to the pump in the IV delivery system to begin delivery of the intravenous liquid through the fluid line.

Step 504 includes placing the fluid flow in contact with the membrane separating the liquid chamber from the outer chamber in the gas elimination apparatus. Step 506 includes allowing a gas in the fluid flow to transition through the membrane into the outer chamber. Step 508 includes opening the valve in the outer chamber to vent gas into the atmosphere. In some embodiments, step 508 includes automatically opening the valve when the gas pressure in the outer chamber reaches a threshold value. Step 510 includes delivering the fluid flow through the fluid outlet of the gas elimination apparatus.

Step 512 may further include determining a gas elimination rate. In some embodiments, step 512 may include counting a number of bubbles per unit cross-sectional area per unit time along the fluid line, downstream of the gas elimination device using the bubble sensor. In some embodiments, step 512 further includes counting the number of bubbles per unit cross-sectional area per unit time along the fluid line, upstream of the gas elimination apparatus using another bubble sensor. In yet other embodiments, step 512 includes measuring a bubble size and estimating a total gas volume flow rate using data provided by the bubble sensor.

Step 514 includes adjusting a fluid flow parameter based on the gas elimination rate. In some embodiments, step 514 may include providing a command to the pump to reduce or increase a flow rate, using the controller. In some embodiments, step 514 may include increasing a temperature setting of the thermostat when the gas elimination rate is greater than a threshold value. In some embodiments, step 514 may include reducing the temperature setting of the thermostat when the gas elimination rate is lower than a second threshold value. In some embodiments, step 514 includes providing an alarm to a centralized system when a bubble count in sensor 182 becomes higher than a first threshold, or when the bubble elimination rate becomes lower than a second threshold.

Figure 6A:
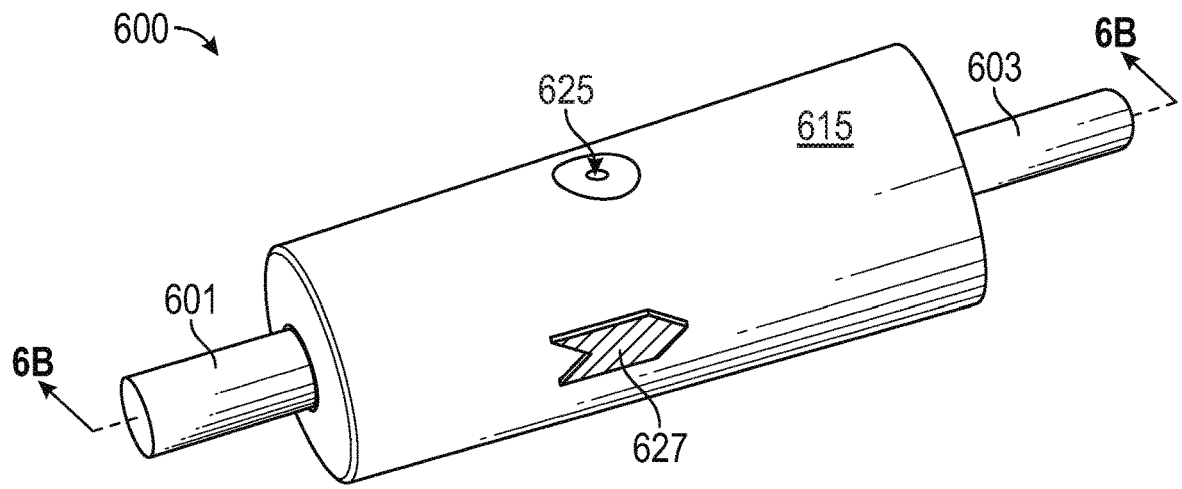
FIG. 6A illustrates a perspective of a gas elimination apparatus for use in an IV delivery system, according to some embodiments.

FIG. 6A illustrates a perspective of a gas elimination apparatus 600 for use in an IV delivery system, according to some embodiments. A wall 615 protects and provides structural support to the apparatus. Wall 615 may include a flow indicator 627 point from a fluid inlet 601 to a fluid outlet 603. A gas venting valve 625 allows excess gas to vent out of the apparatus from the fluid within wall 615.

In some embodiments, valve 625 may be an umbrella valve located on the cylindrical portion of the device, as shown. Some embodiments may include additional umbrella valves at other locations. In some embodiments, as shown, the shape of gas elimination apparatus 600 is slightly tapered such that the circular cross-section at fluid outlet 603 is larger than the circular cross-section at fluid inlet 601. This taper could also be reversed such that the larger end is fluid inlet 601 and the smaller end is fluid outlet 603. A tapered shape may facilitate manufacturing of the gas elimination apparatus 600.

Figure 6B:
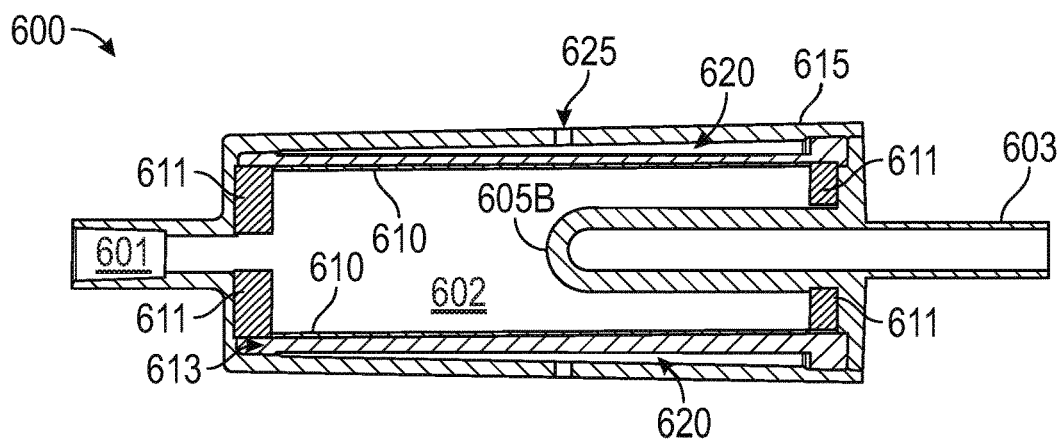
FIG. 6B illustrates a cross-section of a gas elimination apparatus for use in an IV delivery system, according to some embodiments.
Figure 6C:
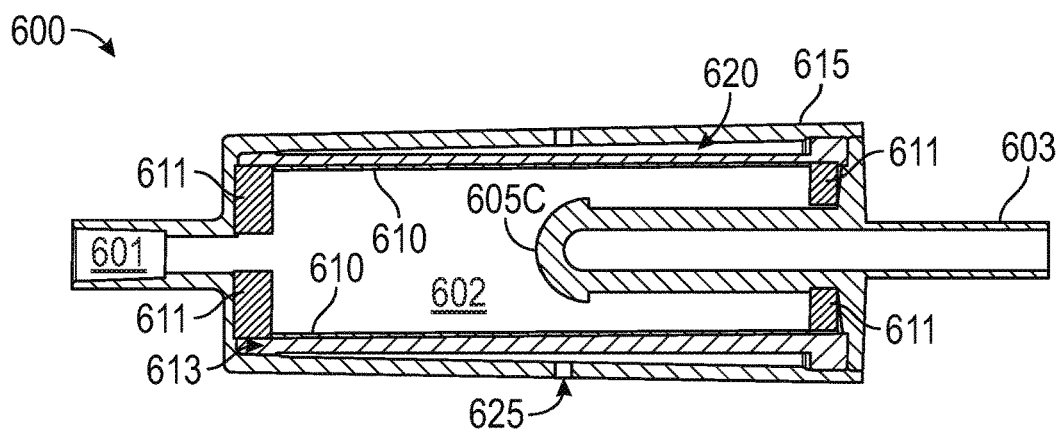
FIG. 6C illustrates a cross-section of a gas elimination apparatus for use in an IV delivery system, according to some embodiments.

FIGS. 6B-C illustrate a longitudinal cross-section of gas elimination apparatus 600 including a flow diversion member 605B, C and a support cage 613 to provide structural support to a membrane 610, according to some embodiments. Membrane 610 may be as any water impermeable membrane as described above membranes 210 or 211, cf. FIG. 2 and the description thereof). Gas elimination apparatus 600 includes liquid chamber 602, fluidly coupled with fluid inlet 601 and with fluid outlet 603. Membrane 610 separates liquid chamber 602 from an outer gas chamber 620. Outer gas chamber 620 is fluidly coupled to ambient through valve 625, which may be a one-way valve (e.g., umbrella valve). As liquid enters gas elimination apparatus 600 through fluid inlet 601, any gas bubbles or gas volumes present in the liquid will either rise up to membrane 610 under their own buoyancy or be deflected toward membrane 610 by a flow diversion member 605B, C. When gas elimination apparatus 600 is oriented with its longitudinal axis perpendicular to gravity, bubbles will rise under buoyancy or be deflected by flow diversion member 605B or 605C and arrive at the apex of the circular cross-section of fluid chamber 602 to contact membrane 610. When gas elimination apparatus 600 is oriented with its longitudinal axis parallel to gravity, then bubbles will rise or be deflected to end walls 611. Once there, the bubbles will accumulate until they form a gas layer in contact with membrane 610, at which point they will vent to outer chamber 620. Flow diversion member 605B is spherically shaped with a cut out section facing fluid outlet 603, such that the member 605B can have a crescent or umbrella shape as shown in FIG. 2D, having a concave internal surface on an opposing side of the member 605B as a convex outer surface. The spherical shape is illustrated on the front end of the member 605B in FIG. 6B. In some embodiments, the apparatus 600 can have a flow diversion member 605C that is half-spherically shaped, such that the member 605C has a mushroom shape, as depicted in FIG. 6C. In some embodiments, the mushroom shape member 605C can also have a concave internal surface, similar to that shown for member 605B. In some embodiments, the mushroom shape member 605C can have a planar internal surface.

Outer chamber 620 is annular in cross-section and is contiguous from inlet to outlet (i.e., not partitioned by ribs or protrusions). Note as well that according to some embodiments there are no membrane surfaces on the cylinder end walls 611, which are substantially impermeable to gas and liquid. Accordingly, gas venting occurs through the cylindrical membrane, as the venting valve location is on the cylindrical section. Furthermore, in embodiments consistent with gas elimination apparatus 600, flow diversion members 605B and 605C are supported by fluid outlet 603, rather than by support cage 613 (see, e.g., flow diversion member 205 and support cage 213, and FIGS. 2A-H).

Figure 6D:
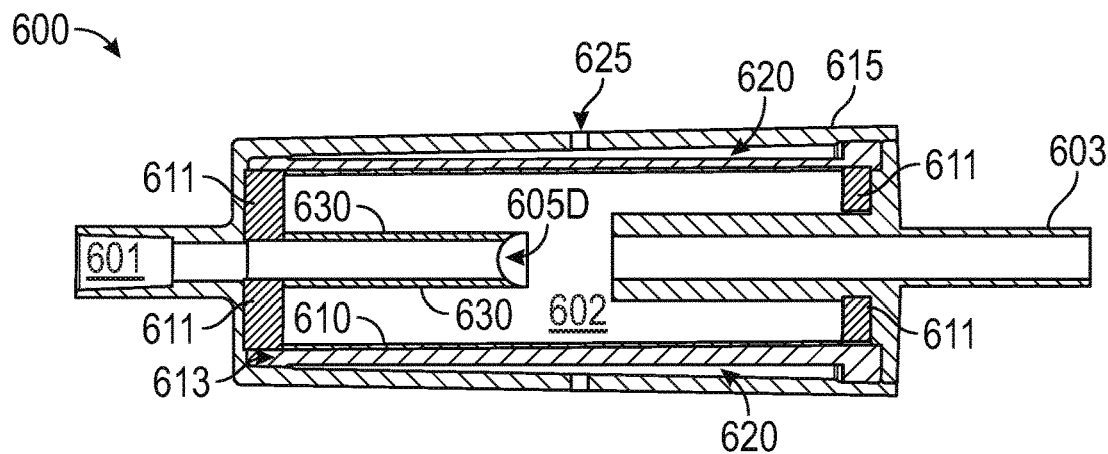
FIG. 6D illustrates a cross-section of a gas elimination apparatus for use in an IV delivery system, according to some embodiments.

FIG. 6D illustrates a longitudinal cross-section of gas elimination apparatus 600 including a flow diversion member 605D, support cage 613, membrane 610, and at least two struts or elongate members 630, according to some embodiments. Struts or elongate members 630 may be supported by fluid inlet 601. In some embodiments, the flow would be diverted around the flow diversion member 605D by following flow paths into and out of the page when referencing FIG. 6D. Flow diversion member 605D may have any of the shapes described above (see FIGS. 2C-H and FIGS. 6B-C). Generally, it is desirable that flow diversion member 605D have a cutout, convex, concave, or flat portion facing fluid outlet 603, and a rounded, or convex portion facing fluid inlet 601. In some embodiments, it is also desirable that struts or elongate members 630 extend generally along the flow direction into liquid chamber 602 to provide the least flow resistance. All other elements in FIG. 6D are as described above in relation to FIGS. 6A-C and having the same reference numerals.

Figure 7A:
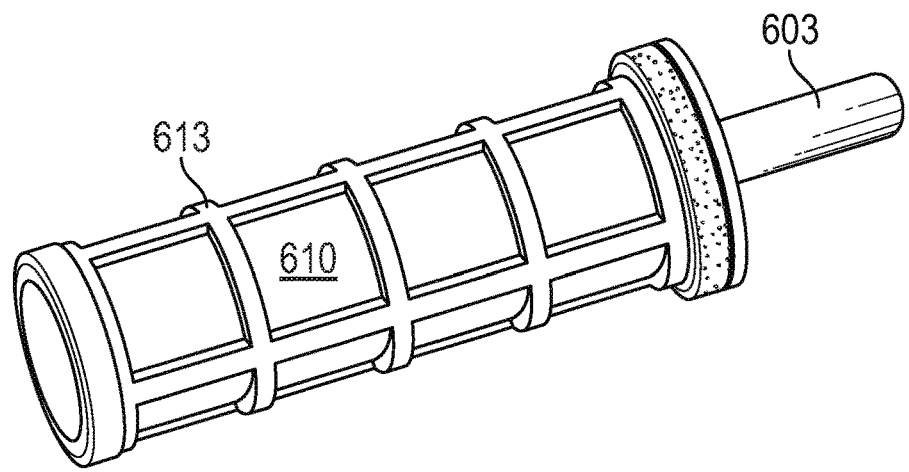
FIG. 7A illustrates a support cage including a membrane, according to some embodiments.

FIG. 7A illustrates support cage 613 including a membrane 610, according to some embodiments. Membrane 610 is either attached to the interior surface of support cage 613 or to the exterior surface of support cage 613. In some embodiments, membrane 610 may be embedded into the structure of support cage 613. Accordingly, membrane 610 forms a barrier between liquid chamber 602 and outer gas chamber 620 through which only gases may pass. Furthermore, in some embodiments, membrane 610 may be welded or heat-bonded to support cage 613. In some embodiments, membrane 610 may be insert-molded together with molding support cage 613. Accordingly, the output of the molding process for support cage 613 is a water tight cage with membrane 610 attached.

Figure 7B:
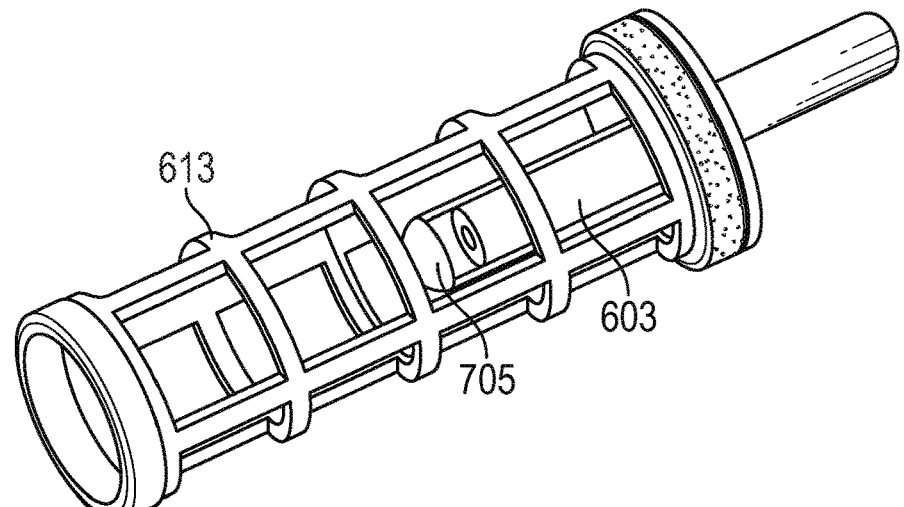
FIG. 7B illustrates the support cage of FIG. 7A including a flow diversion member cutout, according to some embodiments.

FIG. 7B illustrates support cage 613 including a cutout of flow diversion member 705, according to some embodiments. Flow diversion member 705, as illustrated here, is a spherical diverter and may include a cutout facing fluid outlet 603, as illustrated.

Figure 7C:
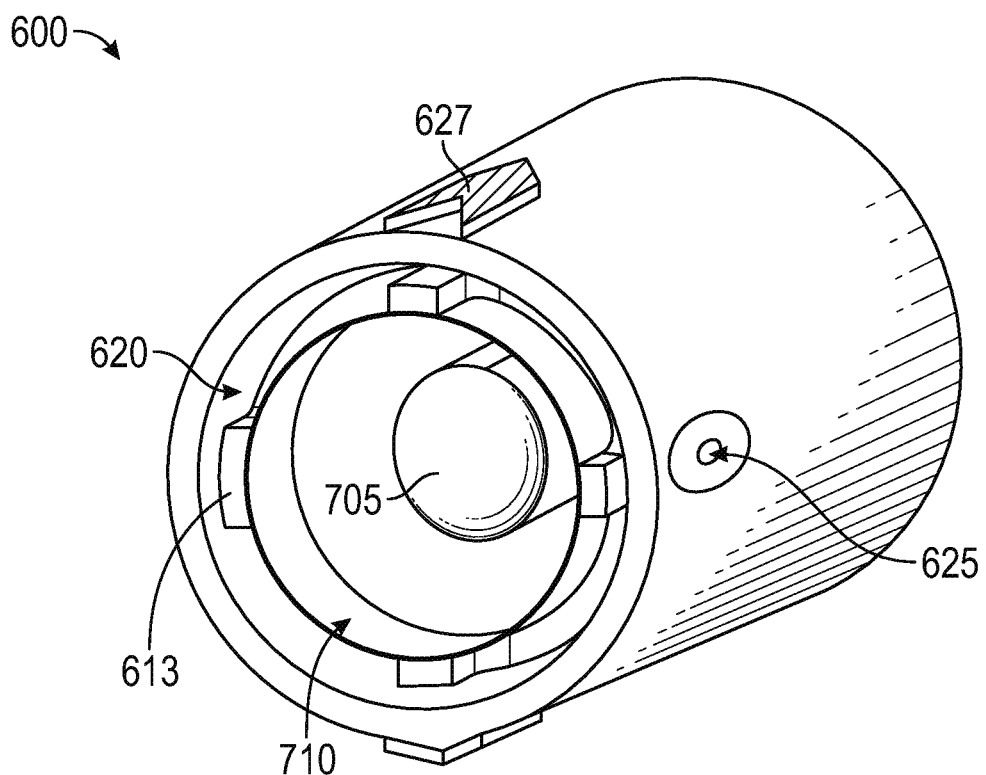
FIG. 7C illustrates a cross-section of a gas elimination apparatus with a flow diversion member, according to some embodiments.

FIG. 7C illustrates a cross-section of gas elimination apparatus 600 with flow diversion member 705 (see FIG. 7B), according to some embodiments. FIG. 7C presents a view of flow diversion member 705 as the flow would see it from fluid inlet 601 toward fluid outlet 603.

Figure 7D:
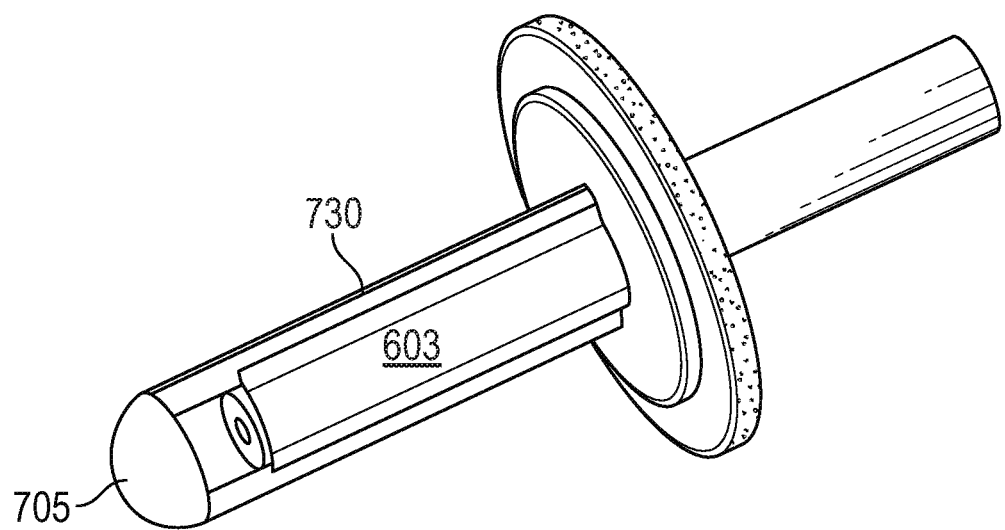
FIG. 7D illustrates a perspective of a flow diversion member used in a gas elimination apparatus, according to some embodiments.

FIG. 7D illustrates a perspective of flow diversion member 705 used in gas elimination apparatus 600 (for example, see FIG. 6), according to some embodiments. FIG. 7D shows a view of flow diversion member 705 integrated into fluid outlet 603. Bubbles which are able to follow streamlines which approach flow diversion member 705 are directed radially out towards membrane 610 (see FIG. 7C) where they are captured, thus reducing their ability to flow into fluid outlet 603 and continue immersed in the fluid flow downstream from gas elimination apparatus 600. Flow diversion member 705 is attached to fluid outlet 603 by, for example, two struts 730 (more or fewer struts may also be used), or elongate members, which extend out from fluid outlet 603. Accordingly, struts 730 are occluded from the fluid flow coming from fluid inlet 601 by flow diversion member 705.

Figure 7E:
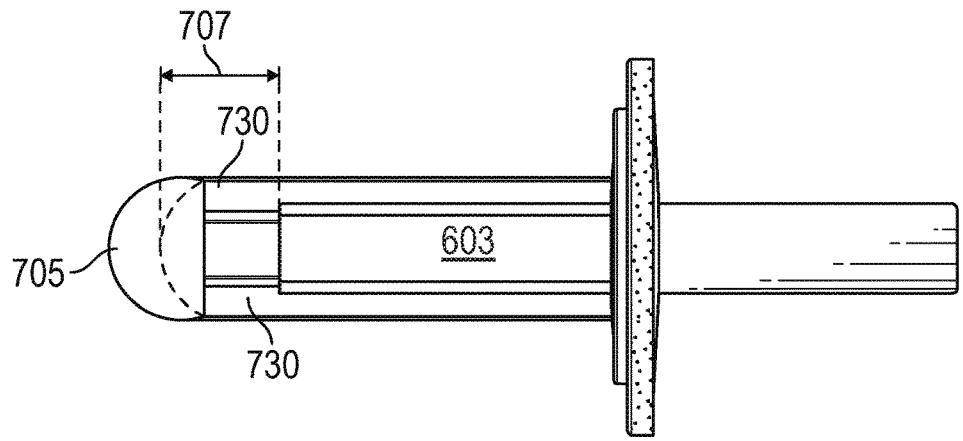
FIG. 7E illustrates a side view of the flow diversion member of FIG. 7D, according to some embodiments.

FIG. 7E illustrates a side view of flow diversion member 705, according to some embodiments. In some embodiments, and without limitation, a distance 707 from fluid outlet 603 to the far side of the cutout is approximately 6 mm. For a perspective, in some embodiments the overall size of gas elimination device 600 may be approximately 40-50 mm in length, and 14-17 mm in diameter.

Figure 8A:
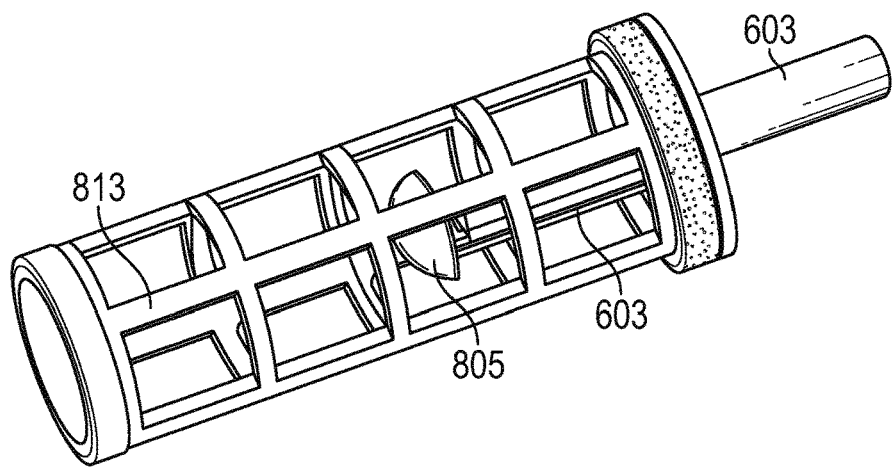
FIG. 8A illustrates a support cage of a gas elimination apparatus, including a flow diversion member cutout, according to some embodiments.

FIG. 8A illustrates a support cage 813 of gas elimination apparatus 600, including a flow diversion member 805, according to some embodiments. Flow diversion member 805 is spherical, being substantially half-spherical, wherein the flat-side of the half-sphere faces fluid outlet 603. This shape is similar to other shapes described herein as having a mushroom shape. Bubbles which follow streamlines that bring them to flow diversion member 805 are deflected radially out towards membrane 610 (not shown for clarity). The abrupt absence of diversion surface where the sphere is cut makes it difficult for deviating bubbles to turn towards fluid outlet 603, thus increasing the likelihood of their capture at membrane 610.

Figure 8B:
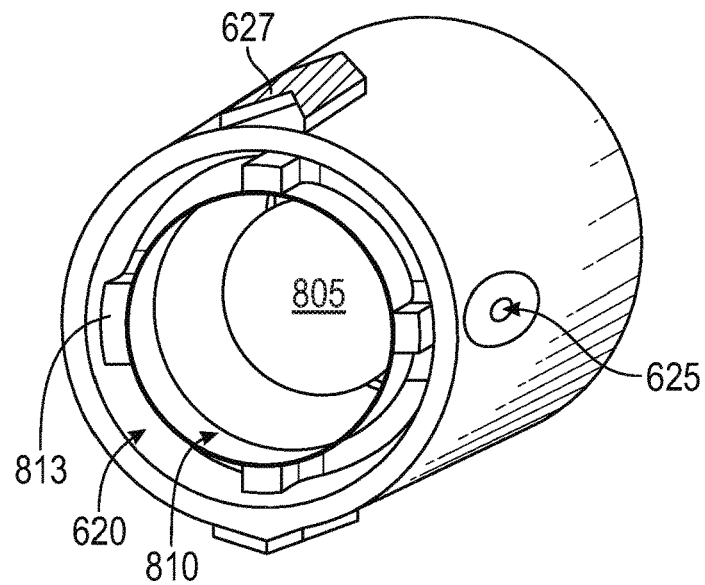
FIG. 8B illustrates a cross-section of a gas elimination apparatus with a flow diversion member, according to some embodiments.

FIG. 8B illustrates a cross-section of gas elimination apparatus 600 with flow diversion member 805, according to some embodiments. FIG. 8B presents a view of the flow diversion member 805 as the flow would see it moving from fluid inlet 601 toward fluid outlet 603.

Figure 8C:
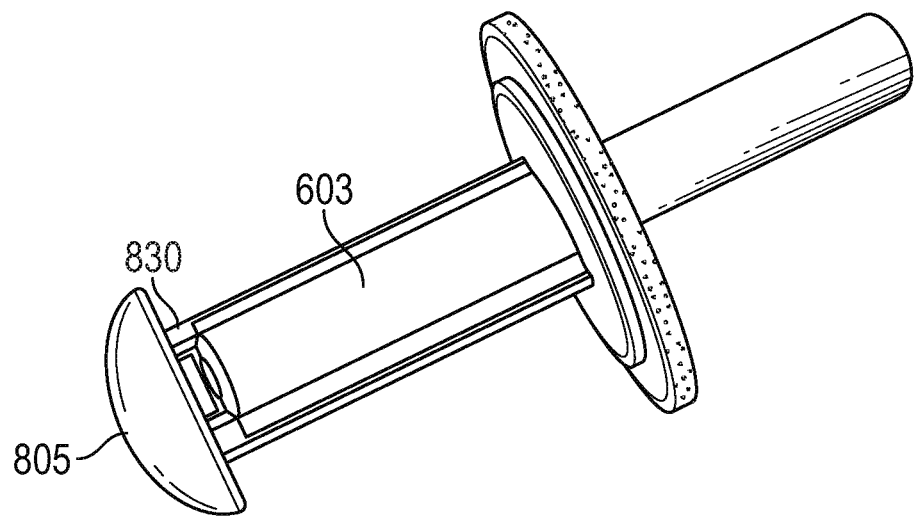
FIG. 8C illustrates a perspective of a flow diversion member used in a gas elimination apparatus, according to some embodiments.
Figure 8D:
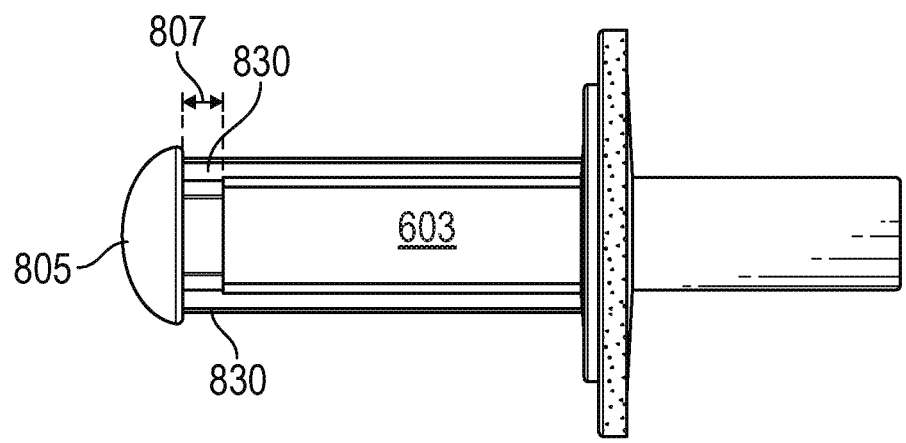
FIG. 8D illustrates a side view of the flow diversion member of FIG. 8C, according to some embodiments.

FIGS. 8C-D illustrate a perspective of flow diversion 805, according to some embodiments. FIG. 8C illustrates struts 830 coupling flow diversion member 805 with fluid outlet 603. In some embodiments, the distance 807 between the flat face of flow diversion member 805 and fluid outlet 603 is approximately 1.5 mm.

Figure 9A:
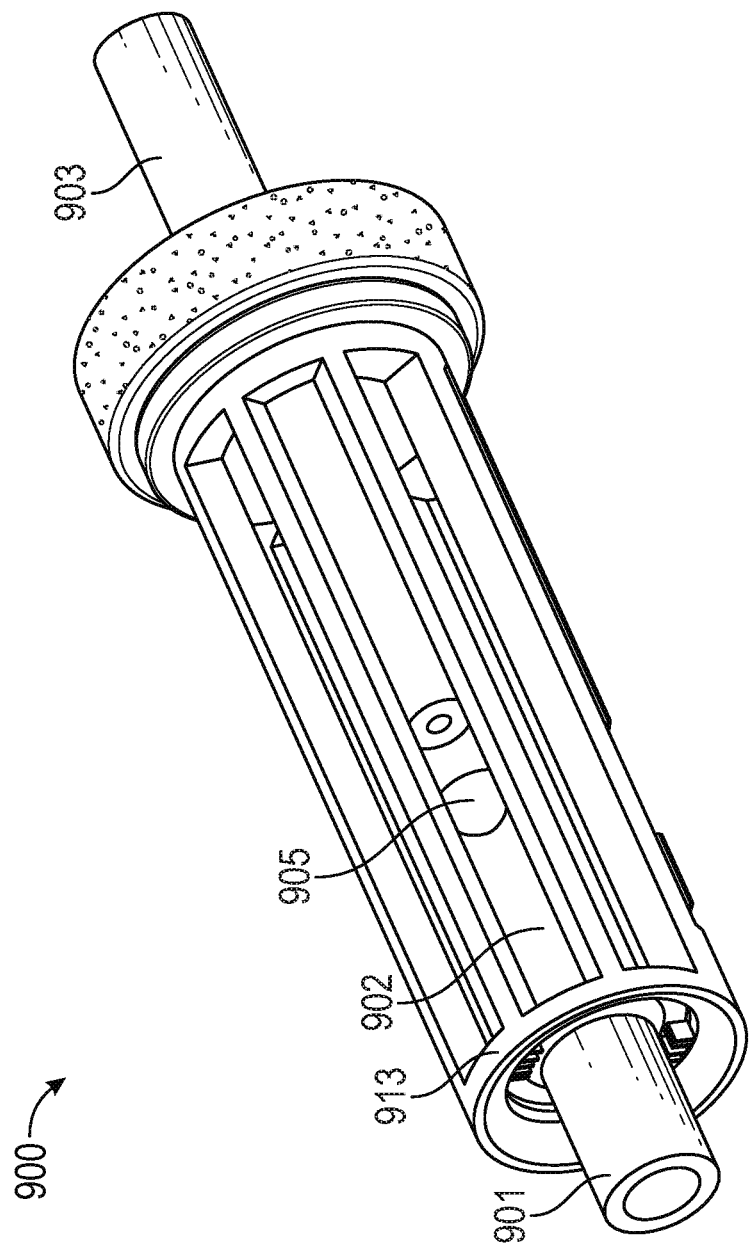
FIG. 9A illustrates a perspective of a support cage for a gas elimination apparatus including a flow diversion member cutout, according to some embodiments.
Figure 9B:
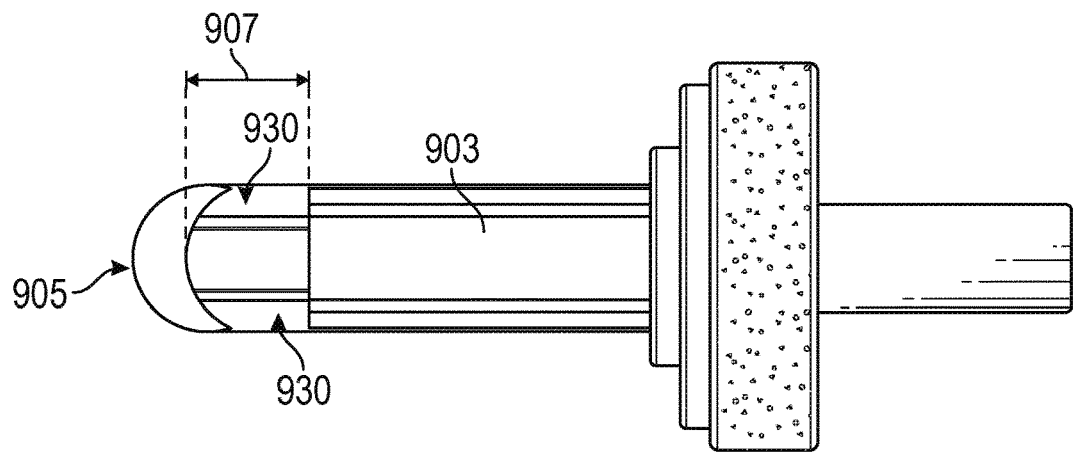
FIG. 9B illustrates a top view of the flow diversion member of FIG. 9A, according to some embodiments.
Figure 9C:
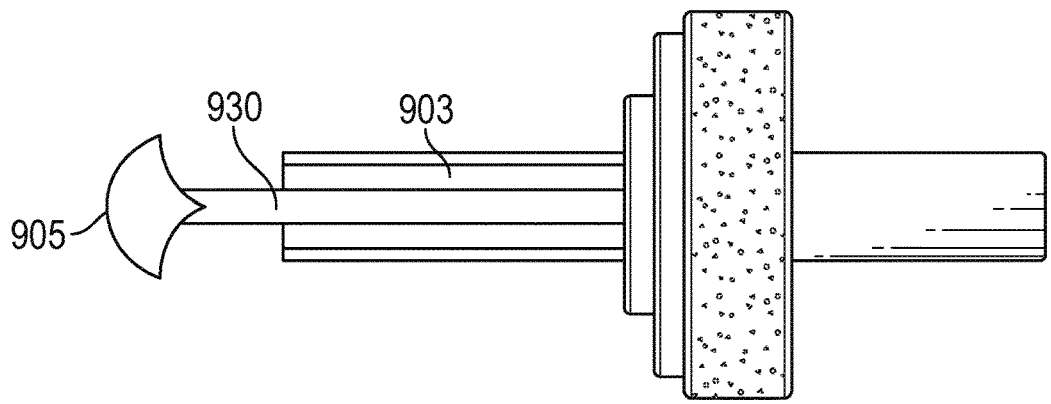
FIG. 9C illustrates a side view of the flow diversion member of FIG. 9A, according to some embodiments.

FIGS. 9A-C illustrate perspective, top, and side views of support cage 913 for a gas elimination apparatus 900, respectively. Support cage 913 incorporates lengthwise struts to support membrane 610. In gas elimination apparatus 900, membrane 610 may be attached to the outside support cage 913, Gas elimination apparatus 900 includes a flow diversion member 905 with a cutout facing fluid outlet 903 at a distance 907 of approximately 6 mm, according to some embodiments. A fluid inlet 901 lets an IV fluid to flow inside a liquid chamber 902 delimited by support cage 913. The flow diversion member 905 can have multiple inwardly facing concave surfaces when viewed from the side (as in FIG. 9C) and an umbrella-shape when viewed from the top (as in FIG. 9B).

Figure 10A:
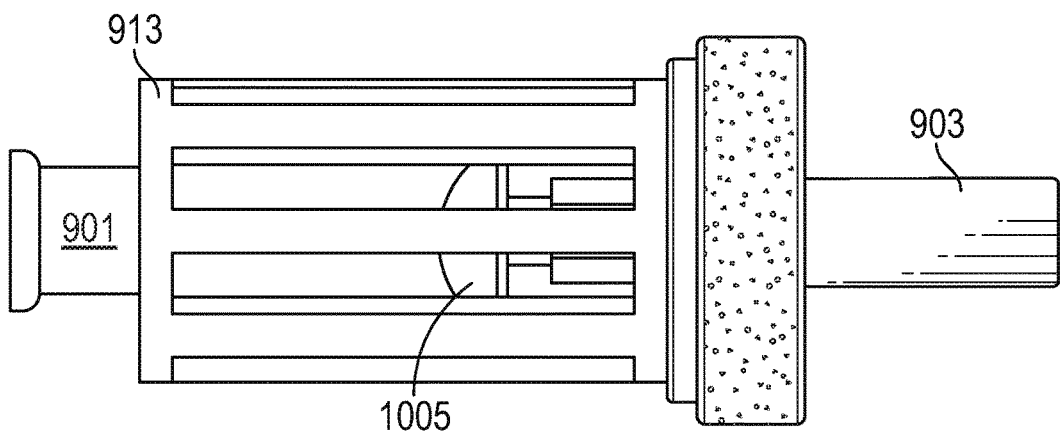
FIG. 10A illustrates a side view of a support cage for a gas elimination apparatus including a flow diversion member cutout, according to some embodiments.

FIG. 10A illustrates a side view of support cage 913 for a gas elimination apparatus 900 including a flow diversion member 1005 having a semi-spherical shape, such as a mushroom, according to some embodiments.

Figure 10B:
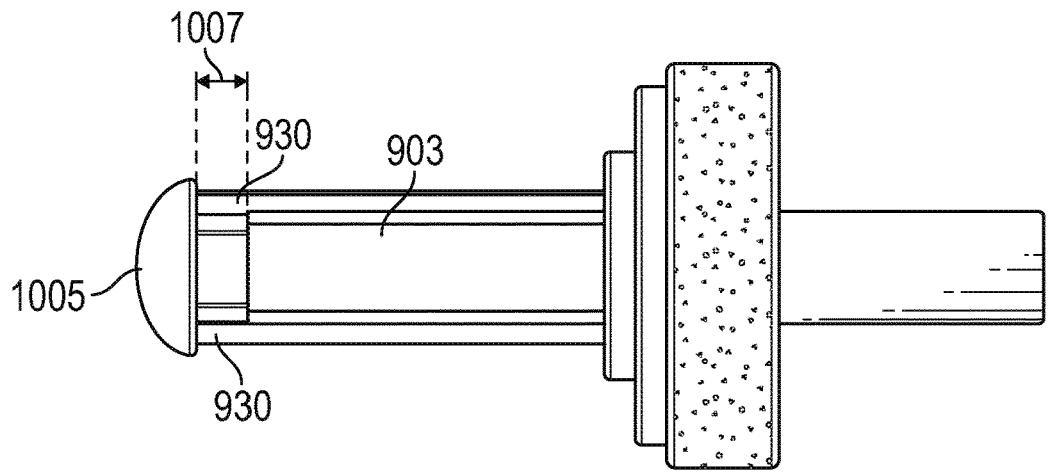
FIG. 10B illustrates a top view of the flow diversion member of FIG. 1.0A, according to some embodiments.
Figure 10C:
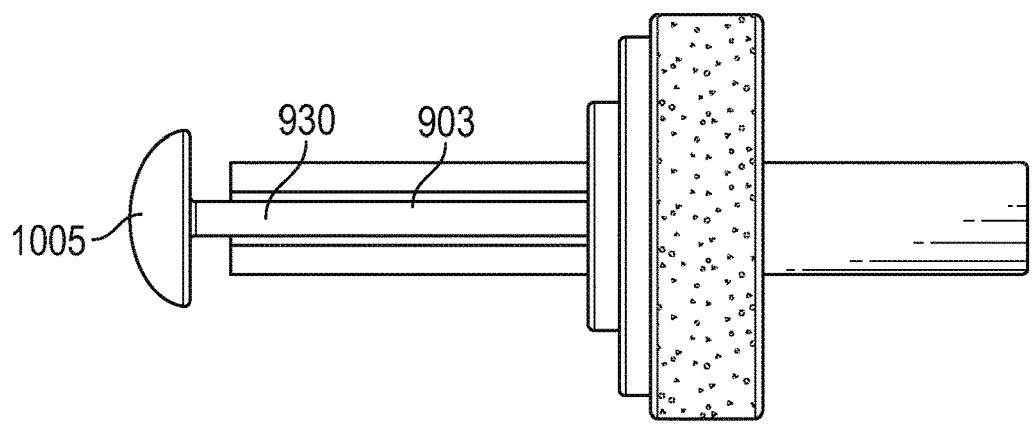
FIG. 10C illustrates a side view of the flow diversion member of FIG. 10A, according to some embodiments.

FIGS. 10B-C illustrate top and side views of flow diversion member 1005, respectively. Accordingly, a flat side in flow diversion member 1005 may be disposed at a distance 1007 of approximately 6 mm from fluid outlet 603, according to some embodiments.

Figure 11:
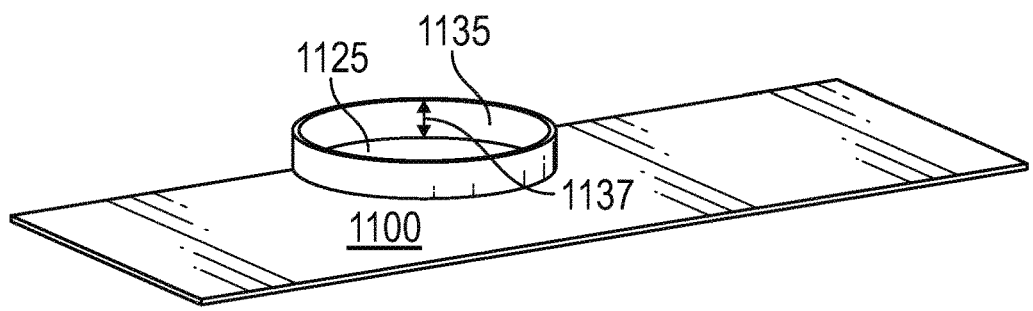
FIG. 11 illustrates a gas venting valve for use in a gas elimination apparatus, according to some embodiments.

FIG. 11 illustrates a gas venting valve 1125 for use in a gas elimination apparatus 1100, according to some embodiments. Gas venting valve 1125 may be an umbrella valve; the surface of gas elimination apparatus 1100 where the umbrella valve sits when in the closed position may be recessed or surrounded by a ridge or fence 1135 such that if placed in contact with another surface, the umbrella valve itself is not limited from opening under the action of venting of internal air. Fence 1135 has a height 1137 that is at least as high as the travel distance to fully open valve 1125. Furthermore, the surface of the device where the umbrella valve sits when in the closed position may be recessed or surrounded by a ridge or fence such that if placed in contact with another surface, the umbrella valve itself is not limited from opening under the action of venting of internal air.

Figure 12:
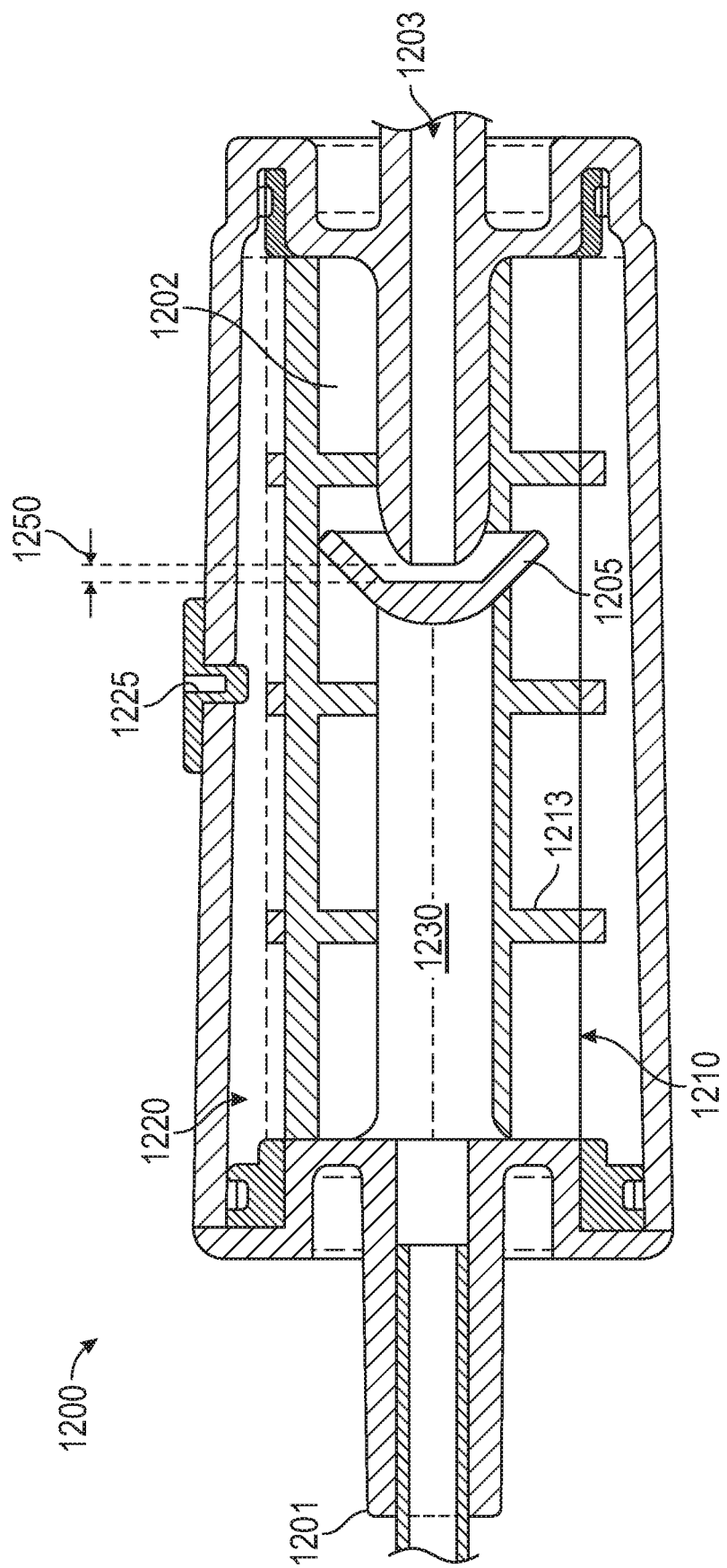
FIG. 12 illustrates a cross-section of a gas elimination apparatus for use in an IV delivery system, according to some embodiments.

FIG. 12 illustrates a longitudinal cross-section of a gas elimination apparatus 1200 for use in an IV delivery system, according to some embodiments. Gas elimination apparatus 1200 includes a fluid inlet 1201 coupling a fluid flow into a liquid chamber 1202. A fluid outlet 1203 protrudes into liquid chamber 1202 to collect and deliver the bubble-deficient fluid. A flow diversion member 1205 proximal to fluid outlet 1203 is configured to block a direct fluid flow between fluid inlet 1201 and fluid outlet 1203. Bubbles in the fluid flow migrate to an outer gas chamber 1220 through a membrane 1210. A support cage 1213 provides structural support to membrane 1210, Membrane 1210 covers a portion of the interior surface of liquid chamber 1202, and separates liquid chamber 1202 from outer chamber 1220. Accordingly, when intravenous liquid 150 comes in contact with membrane 1210, gas bubbles contained in the fluid are allowed to pass through the membrane pores, while water and other solvents or elements in intravenous liquid 150 are contained by membrane 1210 within interior chamber 1202.

Gas elimination apparatus 1200 includes a gas venting valve 1225 fluidically coupling outer gas chamber 1220 with the atmosphere. In some embodiments, gas venting valve 1225 provides protection against air entering gas elimination apparatus 1200 when a pressure gradient is formed from outside (e.g., the atmosphere) to inside (e.g., outer chamber 1220). Under these conditions, gas venting valve 1225 (e.g.

an umbrella valve) will seal outer chamber 1220 to prevent air from entering gas elimination apparatus 1220. Membranes 1210 may include materials having a geometry and other physical properties similar to those described in detail with respect to membranes 210 and 211.

In some embodiments, flow diversion member 1205 is supported by at least one strut or elongate member 1230, according to some embodiments. Strut or elongate member 1230 may extend from fluid inlet 1201. Flow diversion member 1205 may have any of the shapes described above (cf. FIGS. 2C-H and FIGS. 6B-D). In some embodiments, it is also desirable that strut or elongate member 1230 extend generally along the flow direction into liquid chamber 1202 to provide the least flow resistance. Further, a gap 1250 is formed between flow diversion member 1205 and fluid outlet 1203. In some embodiments, it is desirable to extend strut 1230 as far as possible into interior chamber 1202 to reduce gap 1250, without significantly reducing the overall fluid flow from fluid inlet 1201 to fluid outlet 1203. A reduced gap 1250 further enhances the likelihood that even small gas bubbles be trapped inside interior chamber 1202 and eventually diffuse through membrane 1210 into outer gas chamber 1220. Accordingly, any bubbles present in the liquid may be forced to follow a more torturous path from fluid inlet 1201 to fluid outlet 1203. In some embodiments, and without limitation, the gap 1250 may be approximately 1 mm. In some embodiments, the gap 1250 may be as small as 0.5 mm, or even smaller. More generally, the gap may have a dimension that is not smaller than the outlet flow area (e.g., the cross section of fluid outlet 1203). For example, in some embodiments it is preferable that gap 1250 be about 1⁄4 of the diameter of fluid outlet 1203, or greater. In some embodiments used for IV delivery, gap 1250 is desirably greater than at least the diameter of a regular blood cell to avoid any shearing effects on the cells (about 10 micrometers, or more).

Some other desirable features in gas elimination apparatus 1200 may include the flow diversion member 1205 extending radially beyond the diameter of fluid inlet 1201 and fluid outlet 1203, thus forcing the fluid flow to deflect away from the axial direction of gas elimination apparatus 1200 and enhancing the transition of gas bubbles into membrane 1210. Further, in some embodiments flow diversion member 1205 may include a pointed bullet shape center portion having umbrella type extensions spreading radially, wherein the edges of flow diversion member 1205 extend slightly beyond (e.g., downstream or distally of) fluid outlet 1203, thereby forcing the fluid flow to make a double "U-turn" before accessing fluid outlet 1203 (essentially, a 360° turn, or at least a turn of more than 90°). For example, edges of flow diversion member 1205 may extend distally of a proximal end of the fluid outlet 1203, and the proximal end of the fluid outlet 1203 is received within a cavity or umbrella formed by the distally extending edges of the flow diversion member 1205. The cavity or umbrella formed by the distally extending edges of the flow diversion member 1205 may form shapes described above (cf. FIGS. 2C-H and FIGS. 6B-D) or it may form straight and beveled edges in some embodiments.

The configuration of flow diversion member 1205 supported by strut 1230 extending from fluid inlet 1201 may be desirable for ease of manufacturability of gas elimination apparatus 1200. For example, when flow diversion member 1205 is supported from fluid outlet 1203, there is a limit for gap 1250, wherein tolerances of manufacture techniques for such a device add up unfavorably to have a minimum gap distance. In some embodiments, the size of a molding tool used to manufacture gas elimination apparatus 1200 may prevent the size of gap 1250 from being smaller than a limiting value.

Figure 13A:
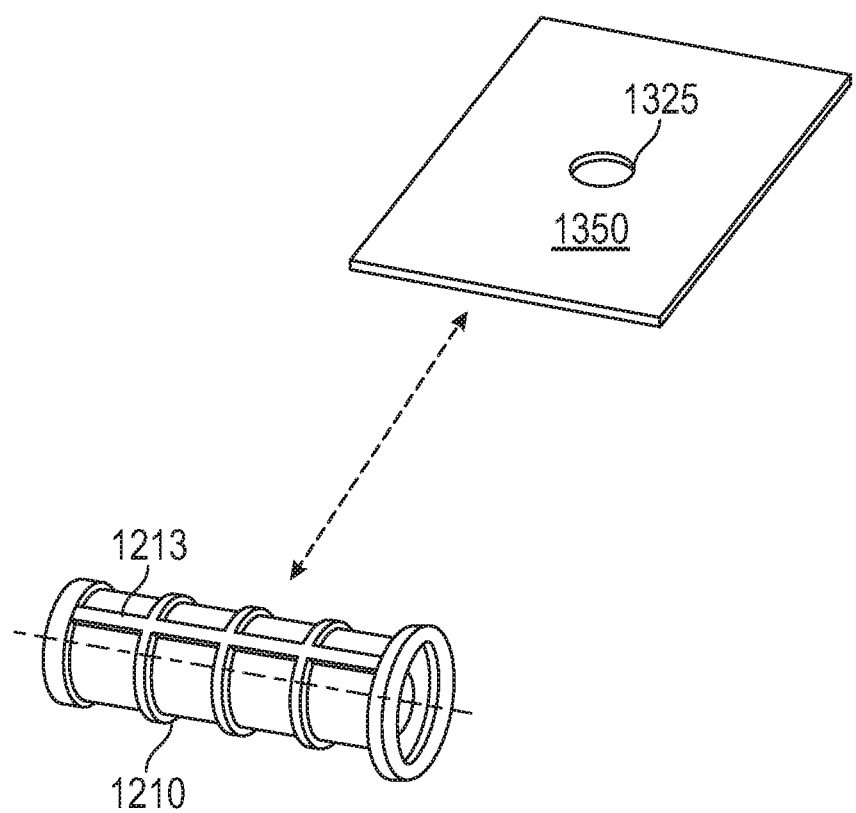
FIG. 13A illustrates a perspective of a support cage for a gas elimination apparatus including an absorbent element in the outer gas chamber, according to some embodiments.

FIG. 13A illustrates a perspective of support cage 1213 for a gas elimination apparatus including an absorbent element 1350 in the outer gas chamber (e.g., any one of gas elimination apparatuses 100, 200, 200A-C, 400, 600, and 1200, and any one of outer gas chambers 220, 620, 1220), according to some embodiments. In some embodiments, the gas elimination apparatus eliminates gas from both heated and unheated IV fluids. In some embodiments, the temperature of the fluid may be approximately 37-42 degrees Celsius. Under these conditions, water vapor may pass across the membrane (e.g., any one of membranes 210, 211, 410, 610, 710, 810, and 1210) due to vaporization of the liquid component of the IV fluids (e.g., water). After passing across the membrane (e.g., any one of outer gas chambers 220, 420, 620, and 1220), the water vapor may condense back to liquid and accumulate in the outer gas chamber (e.g., outer gas chamber 1220), which may be undesirable. For example, when water that accumulates in the outer gas chamber may hinder and constrain the passage of gas through the membrane, or the passage of gas to the relief valve (e.g., any one of valves 225, 625, and 1225) into the atmosphere. Furthermore, the liquid itself may exit the relief valve, potentially creating a contamination hazard, nuisance or inconvenience.

Figure 13B:
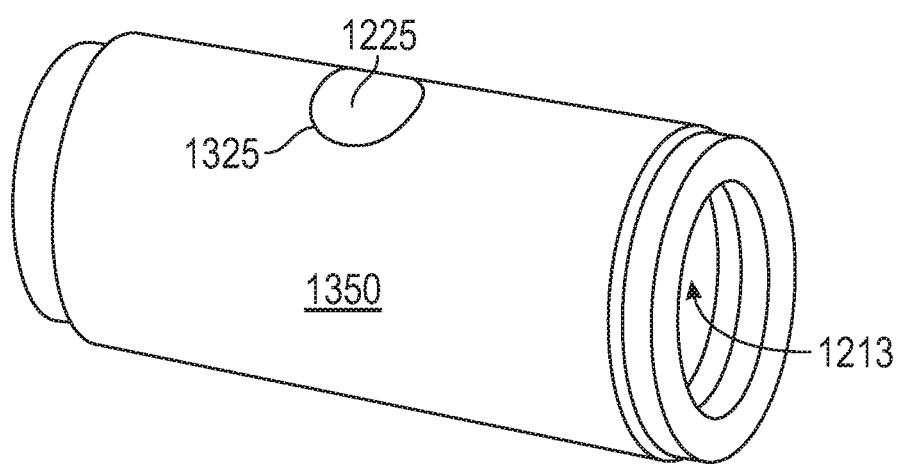
FIG. 13B illustrates a perspective of a support cage for a gas elimination apparatus with the absorbent element surrounding the support cage, according to some embodiments.

To avoid water condensation or any other liquid accumulation in the outer gas chamber, in some embodiments a gas elimination apparatus includes a sheet 1350 of absorbent material placed between the outside of support cage 1213 and the inner wall of the outer gas chamber. In some embodiments, sheet 1350 includes cellulose paper. Without limitation, sheet 1350 may include any material suitable for wicking up or absorbing and holding liquid (e.g. water). In some embodiments, and without limitation, sheet 1350 may include a cotton fiber material or any combination thereof, for absorbing liquids. Further, in some embodiments, sheet 1350 includes an aperture 1325 to open the access to the relief valve or vent. Accordingly, aperture 1325 is disposed directly below the relief valve location, FIG. 13B illustrates a perspective of a support cage 1213 for a gas elimination apparatus with sheet 1350 surrounding support cage 1213, according to some embodiments. Accordingly, aperture 1325 creates an open access to valve 1225 for the gas escaping the outer gas chamber.

Figure 14:
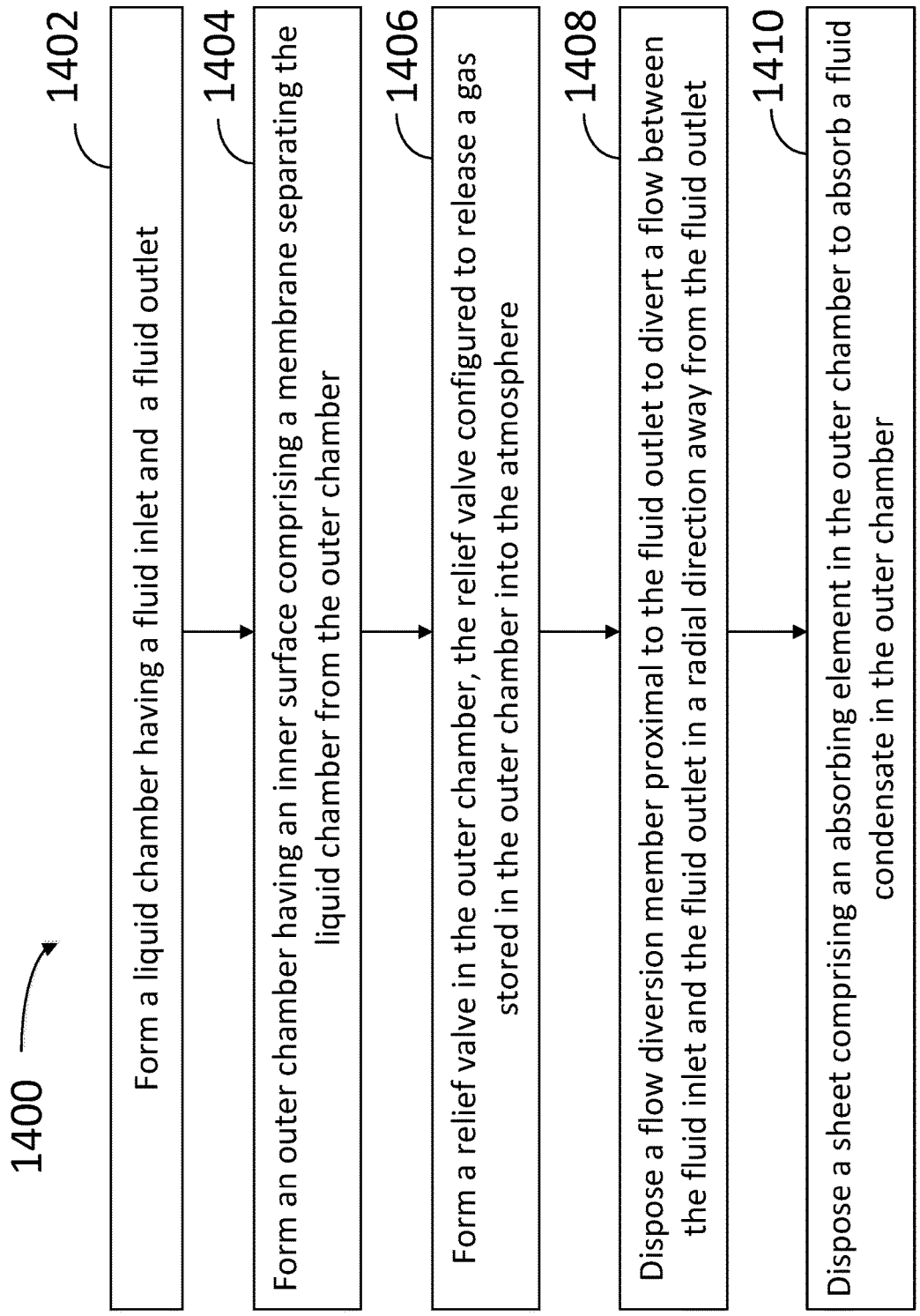
FIG. 14 illustrates a flowchart in a method for manufacturing a gas elimination apparatus for use in an IV delivery system, according to some embodiments.

FIG. 14 illustrates a flowchart in a method 1400 for manufacturing a gas elimination apparatus for use in an IV delivery system, according to some embodiments. Methods consistent with method 1400 may include using a gas elimination apparatus as disclosed herein, having at least one membrane (e.g., gas elimination apparatus 100, 200, 200A-C, 400 and 1200, and membranes 210, 211, 410 and 1210, cf. FIGS. 1, 2A-H, 3A-C, 4A and 12, respectively). Further according to some embodiments, methods consistent with the present disclosure may include an IV delivery system as disclosed herein. The IV delivery system may include a frame, a fluid container, a pump, a thermostat, a fluid line, an antenna, at least a bubble sensor, and a valve as disclosed herein (e.g., frame 140, fluid container 143, pump 145, fluid line 130, antenna 155, bubble sensors 181 and 182, and valve 190, cf. FIG. 1).

Further according to some embodiments, methods consistent with method 1400 may include at least one, but not all, of the steps illustrated in FIG. 14. Moreover, in some embodiments a method as disclosed herein may include steps in method 1400 performed in a different sequence than that illustrated in FIG. 14. For example, in some embodiments at least two or more of the steps in method 1400 may be performed overlapping in time, or even simultaneously, or quasi-simultaneously.

Step 1402 includes forming a liquid chamber having a fluid inlet and a fluid outlet.

Step 1404 includes forming an outer chamber having an inner surface comprising a membrane separating the liquid chamber from the outer chamber. In some embodiments, step 1404 further includes molding the membrane in a support cage in the liquid chamber. In some embodiments, step 1404 further includes heat-bonding the membrane to a support cage in the liquid chamber. In some embodiments, step 1404 further includes welding the membrane into a support cage in the liquid chamber.

Step 1406 includes forming a relief valve in the outer chamber, the relief gas configured to release a gas stored in the outer chamber into the atmosphere.

Step 1408 includes disposing a flow diversion member proximal to the fluid outlet to divert a flow between the fluid inlet and the fluid outlet in a radial direction away from the fluid outlet. In some embodiments, step 1408 includes supporting the flow diversion member by a strut extending from the fluid inlet. In some embodiments, step 1408 includes forming a gap between the flow diversion member and the fluid outlet that is larger than a size of a human red-blood cell. In some embodiments, step 1408 includes forming a gap between the flow diversion member and the fluid outlet that is larger than a tolerance for a length of the fluid inlet and a tolerance for a length of the fluid outlet.

In some embodiments, at least one of steps 1402, 1404, 1406, and 1408 may include printing at least a portion of the material to form the liquid chamber, the outer gas chamber, the relief valve or the flow diversion member with a three-dimensional printer.

Step 1410 includes disposing a sheet comprising an absorbing element in the outer chamber to absorb a fluid condensate in the outer chamber. In some embodiments, step 1410 includes wrapping the sheet around the membrane, in the outer chamber.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. AU structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. An apparatus, comprising:
   a fluid inlet coupling a fluid flow into a liquid chamber;
   a fluid outlet protruding into the liquid chamber;
   a flow diversion member proximal to the fluid outlet, the flow diversion member configured to block a direct flow between the fluid inlet and the fluid outlet;
   a membrane separating a portion of the liquid chamber from an outer chamber, the membrane configured to allow a gas to pass through;
   a gas venting valve fluidically coupling the outer chamber with an atmosphere, wherein the flow diversion member is mechanically supported by an elongate member extending along a flow direction into the liquid chamber; and
   an absorbing element in the outer chamber, the absorbing element configured to absorb a fluid condensate in the outer chamber.

2. The apparatus of claim 1, further comprising a support cage in the liquid chamber to provide mechanical support to the membrane.

3. The apparatus of claim 2, wherein the membrane is disposed on an inner face of the support cage, between the liquid chamber and the support cage.

4. The apparatus of claim 2, wherein the membrane is disposed on an outer face of the support cage, between the support cage and the outer chamber.

5. The apparatus of claim 2, wherein the membrane is embedded in the support cage by molding.

6. The apparatus of claim 1, further comprising a wall perpendicular to a longitudinal axis of the liquid chamber, the wall configured to be impermeable to a fluid in the liquid chamber and to the gas in the liquid chamber.

7. The apparatus of claim 1, wherein the liquid chamber comprises a cylinder with a longitudinal axis aligned with the fluid inlet and the fluid outlet, and further wherein a cross section of the cylinder tapers toward the fluid outlet.

8. The apparatus of claim 1, wherein the flow diversion member comprises a spherical surface having a concave cutout portion facing the fluid outlet.

9. The apparatus of claim 1, wherein the flow diversion member comprises a semi-spherical surface having a flat portion facing the fluid outlet.

10. The apparatus of claim 1, wherein the elongate member comprises a strut that is occluded from the fluid flow by the flow diversion member.

11. The apparatus of claim 1, further comprising a wall surrounding the outer chamber, the wall including a fence around the gas venting valve, the fence configured to prevent an external object to exert pressure on the valve.

12. The apparatus of claim 1, wherein the elongate member is supported by one of the fluid inlet or the fluid outlet.

13. The apparatus of claim 1, wherein a gap between the flow diversion member and the fluid outlet is larger than about 0.5 mm.

\* \* \* \* \*